United States Patent
Allred et al.

(10) Patent No.: US 6,860,736 B2
(45) Date of Patent: Mar. 1, 2005

(54) ORAL TREATMENT DEVICES THAT INCLUDE A THIN, FLEXIBLE BARRIER LAYER AND AN ENDOSKELETON TREATMENT OR ADHESIVE COMPOSITION

(75) Inventors: Peter M. Allred, Riverton, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/790,446

(22) Filed: Feb. 19, 2004

(65) Prior Publication Data

US 2004/0241620 A1 Dec. 2, 2004

Related U.S. Application Data

(63) Continuation-in-part of application No. 10/446,235, filed on May 27, 2003, and a continuation-in-part of application No. 10/637,237, filed on Aug. 8, 2003, and a continuation-in-part of application No. 10/646,484, filed on Aug. 22, 2003, and a continuation-in-part of application No. 10/692,117, filed on Oct. 22, 2003, and a continuation-in-part of application No. 10/701,788, filed on Nov. 4, 2003, and a continuation-in-part of application No. 10/444,242, filed on May 23, 2003.

(51) Int. Cl.[7] ............................. A61C 17/00; A61C 5/00
(52) U.S. Cl. ........................................ 433/80; 433/215
(58) Field of Search .................... 433/80, 215, 216; 424/53; 206/63.5, 369

(56) References Cited

U.S. PATENT DOCUMENTS

| | | | |
|---|---|---|---|
| 165,584 A | 7/1875 | Hopfen |
| 1,637,153 A | 7/1927 | Lawton |
| 2,257,709 A | 9/1941 | Anderson |
| 2,835,628 A | 5/1958 | Saffir |
| 3,339,547 A | 9/1967 | Drabkowski |
| 3,527,219 A | 9/1970 | Greenberg |
| 3,624,909 A | 12/1971 | Greenberg |
| 3,688,406 A | 9/1972 | Porter et al. |
| 3,955,281 A | 5/1976 | Weitzman |
| 4,064,628 A | 12/1977 | Weitzman |
| 4,138,814 A | 2/1979 | Weitzman |
| RE33,093 E | 10/1989 | Schiraldi et al. |

(List continued on next page.)

*Primary Examiner*—Cary E. O'Connor
(74) *Attorney, Agent, or Firm*—Workman Nydegger

(57) ABSTRACT

Oral treatment devices include a barrier layer and an oral treatment composition, and optionally an auxiliary adhesive composition, that acts as an endoskeleton so as to at least partially contribute to maintaining the barrier layer in the shape of a dental tray, or in a tray-like configuration, prior to use. The barrier layer protects the oral treatment and/or adhesive composition from saliva or moisture during use. The treatment and/or auxiliary adhesive compositions can have a consistency ranging from a sticky, viscous gel or a solid. They preferably include a tissue adhesion agent comprising a hydrophilic polymer.

32 Claims, 10 Drawing Sheets

U.S. PATENT DOCUMENTS

| | | |
|---|---|---|
| 4,900,721 A | 2/1990 | Bansemir et al. |
| 4,902,227 A | 2/1990 | Smith |
| 5,008,093 A | 4/1991 | Merianos |
| 5,085,585 A | 2/1992 | Zimble |
| 5,108,742 A | 4/1992 | Merianos |
| 5,112,225 A | 5/1992 | Diesso |
| 5,183,901 A | 2/1993 | Login et al. |
| 5,211,559 A | 5/1993 | Hart et al. |
| 5,310,563 A | 5/1994 | Curtis et al. |
| 5,326,685 A | 7/1994 | Gaglio et al. |
| 5,346,061 A | 9/1994 | Newman et al. |
| 5,356,291 A | 10/1994 | Darnell |
| 5,425,953 A | 6/1995 | Sintov et al. |
| 5,562,449 A | 10/1996 | Jacobs et al. |
| 5,573,399 A | 11/1996 | McClintock, II |
| 5,575,654 A | 11/1996 | Fontenot |
| 5,611,687 A | 3/1997 | Wagner |
| 5,616,027 A | 4/1997 | Jacobs et al. |
| 5,639,445 A | 6/1997 | Curtis et al. |
| 5,702,251 A | 12/1997 | McClintock, II |
| 5,707,235 A | 1/1998 | Knutson |
| 5,711,935 A | 1/1998 | Hill et al. |
| 5,769,633 A | 6/1998 | Jacobs et al. |
| 5,816,802 A | 10/1998 | Montgomery |
| 5,846,058 A | 12/1998 | Fischer |
| 5,863,202 A | 1/1999 | Fontenot et al. |
| 5,879,691 A | 3/1999 | Sagel et al. |
| 5,891,453 A | 4/1999 | Sagel et al. |
| 5,894,017 A | 4/1999 | Sagel et al. |
| 5,895,218 A | 4/1999 | Quinn et al. |
| 5,922,307 A | 7/1999 | Montgomery |
| 5,924,863 A | 7/1999 | Jacobs et al. |
| 5,980,249 A | 11/1999 | Fontenot |
| 5,989,569 A | 11/1999 | Dirksing et al. |
| 6,045,811 A | 4/2000 | Dirksing et al. |
| 6,080,397 A | 6/2000 | Pfirrmann |
| 6,089,869 A | 7/2000 | Schwartz |
| 6,096,328 A | 8/2000 | Sagel et al. |
| 6,106,293 A | 8/2000 | Wiesel |
| 6,126,443 A | 10/2000 | Burgio |
| 6,136,297 A | 10/2000 | Sagel et al. |
| 6,142,780 A | 11/2000 | Burgio |
| 6,155,832 A | 12/2000 | Wiesel |
| 6,183,251 B1 | 2/2001 | Fischer |
| 6,197,331 B1 | 3/2001 | Lerner et al. |
| 6,247,930 B1 | 6/2001 | Chiang et al. |
| 6,274,122 B1 | 8/2001 | McLaughlin |
| 6,277,458 B1 | 8/2001 | Dirksing et al. |
| 6,280,196 B1 | 8/2001 | Berghash |
| 6,287,120 B1 | 9/2001 | Wiesel |
| 6,322,360 B1 | 11/2001 | Burgio |
| 6,331,292 B1 | 12/2001 | Montgomery |
| 6,343,932 B1 | 2/2002 | Wiesel |
| 6,419,903 B1 | 7/2002 | Xu et al. |
| 6,419,906 B1 | 7/2002 | Xu et al. |
| 6,435,873 B1 | 8/2002 | Burgio |
| 6,440,396 B1 | 8/2002 | McLaughlin |
| 6,458,380 B1 | 10/2002 | Leaderman |
| 6,461,158 B1 | 10/2002 | Sagel et al. |
| 6,488,914 B2 | 12/2002 | Montgomery |
| 6,497,575 B2 | 12/2002 | Zavitsanos et al. |
| 6,500,408 B2 | 12/2002 | Chen |
| 6,503,486 B2 | 1/2003 | Xu et al. |
| 6,506,053 B2 | 1/2003 | Wiesel |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,649,147 B1 | 11/2003 | Ye et al. |
| 6,682,721 B2 | 1/2004 | Kim et al. |
| 6,689,344 B2 | 2/2004 | Chang et al. |
| 6,730,316 B2 | 5/2004 | Chen |
| 2001/0046654 A1 | 11/2001 | Zavitsanos et al. ............ 433/32 |
| 2002/0006387 A1 | 1/2002 | Sagel et al. .................... 424/53 |
| 2002/0006388 A1 | 1/2002 | Sagel et al. .................... 424/53 |
| 2002/0012685 A1 | 1/2002 | Sagel et al. .................. 424/401 |
| 2002/0018754 A1 | 2/2002 | Sagel et al. .................... 424/49 |
| 2002/0081555 A1 | 6/2002 | Wiesel ......................... 433/215 |
| 2002/0164292 A1 | 11/2002 | Peterson et al. ............... 424/53 |
| 2002/0182154 A1 | 12/2002 | McLaughlin .................. 424/53 |
| 2002/0187111 A1 | 12/2002 | Xu et al. ....................... 424/53 |
| 2002/0187112 A1 | 12/2002 | Xu et al. ....................... 424/53 |
| 2003/0003421 A1 | 1/2003 | Besenheider et al. ........ 433/215 |
| 2003/0012747 A1 | 1/2003 | Peterson ....................... 424/53 |
| 2003/0036037 A1 | 2/2003 | Zavitsanos et al. .......... 433/215 |
| 2003/0044631 A1 | 3/2003 | Sagel et al. .................. 428/548 |
| 2003/0068284 A1 | 4/2003 | Sagel et al. .................... 424/53 |
| 2003/0068601 A1 | 4/2003 | Zavitsanos et al. .......... 433/215 |
| 2003/0082114 A1 | 5/2003 | Kim et al. ..................... 424/53 |
| 2003/0133884 A1 | 7/2003 | Chang et al. .................. 424/53 |
| 2003/0194382 A1 | 10/2003 | Chang et al. .................. 424/53 |
| 2003/0198606 A1 | 10/2003 | Kim et al. ..................... 424/53 |

ORAL TREATMENT DEVICES THAT INCLUDE A THIN, FLEXIBLE BARRIER LAYER AND AN ENDOSKELETON TREATMENT OR ADHESIVE COMPOSITION

CROSS-REFERENCE TO RELATED APPLICATIONS

This application is a continuation-in-part of co-pending U.S. application Ser. No. 10/446,235, filed May 27, 2003, and a continuation-in-part of co-pending U.S. application Ser. No. 10/637,237, filed Aug. 8, 2003, and a continuation-in-part of co-pending U.S. application Ser. No. 10/646,484, filed Aug. 22, 2003, and a continuation-in-part of co-pending U.S. application Ser. No. 10/692,117, filed Oct. 22, 2003, and a continuation-in-part of co-pending U.S. application Ser. No. 10/701,788, filed Nov. 4, 2003. The foregoing applications are incorporated herein in their entirety. This application is also a continuation-in-part of co-pending U.S. application Ser. No. 10/444,242, filed May 23, 2003.

BACKGROUND OF THE INVENTION

1. The Field of the Invention

The present invention is in the field of oral treatment devices used to treat a person's teeth and/or gums. More particularly, the invention relates to oral treatment devices that include a thin, flexible, moisture-resistant barrier layer and an oral treatment composition and/or auxiliary adhesive composition that acts as an endoskeleton to maintain the barrier layer in a desired configuration prior to use.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another bleaching method involves painting a bleaching composition directly onto a person's teeth. A perceived advantage of paint-on bleaching is that it eliminates the need for a dental tray. The main disadvantage of a paint-on bleaching composition is that it remains directly exposed to the person's saliva and disruptive forces found in a person's mouth. As a result, a significant portion of the bleaching composition does not remain on the teeth where bleaching is desired. Some or all of the composition can dissolve away into the person's saliva and/or be transferred to adjacent oral tissues, potentially irritating soft oral tissues.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces. Like paint-on bleaching compositions, this procedure does not require the use of dental trays. Unlike paint-on bleaching compositions, bleaching strips include a plastic barrier that, at least in theory, keeps the dental bleaching gel from diffusing into the user's mouth.

In reality, because of the generally poor adhesion of bleaching strips to the user's teeth, coupled with their generally flimsy nature, it is often difficult for the user to maintain the bleaching strip in its proper position for the recommended time. Conventional bleaching strips are prone to slip off the teeth as a result of even minimal movement of the user's mouth, jaw or tongue. Indeed, it is recommended that the user not eat, drink, smoke or sleep while wearing the bleaching strip. In practice, it is difficult to talk or smile while properly maintaining the bleaching strip in the correct position.

Even if a user successfully maintains a conventional bleaching strip in its proper position during the recommended bleaching period, the bleaching gel often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

In practical terms, the use of conventional bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are the least prone to move is at night while the person is sleeping. Unfortunately, it is recommended that conventional bleaching strips not be used while sleeping, presumably to prevent accidental choking on an inadvertently dislodged bleaching strip. This confirms the tendency of conventional bleaching strips to easily dislodge from a user's teeth.

Ultimately, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained.

In view of the foregoing, there is an ongoing need for improved treatment apparatus and methods that are simple and easy to use and that reliably remain in position over the user's teeth and/or gums so as to reduce diffusion of the treatment composition into a user's oral cavity. Such improvements would be expected to improve or encourage compliance by the user.

BRIEF SUMMARY OF THE PREFFERED EMBODIMENTS

The present invention relates to oral treatment devices used to treat a person's teeth and/or gums that include a thin, flexible barrier layer and an oral treatment composition and/or auxiliary adhesive composition positioned relative to the barrier layer so as to act as an endoskeleton that is at least partially responsible for maintaining the barrier layer in a desired configuration prior to use (e.g., in the form of a dental tray or tray-like configuration). During use, the barrier layer protects the treatment and/or adhesive compositions from saliva and moisture, which keeps it/them in contact with a person's teeth and/or surrounding soft tissue and helps prevent, minimize or lessen their diffusion into the user's mouth.

The barrier layer is advantageously formed from a moisture-resistant polymer material, examples of which include polyolefins, polyesters, ethylene-vinyl acetate copolymer (EVA), polyurethane, other polymers, and blends thereof (e.g., polyethylene and polypropylene). The barrier layer is advantageously thin and flexible so as to conform to the shape of a person's teeth as a result of the adhesive nature of the oral treatment compositions. The thickness will preferably range from 0.0001 inch to 0.012 inch. It may be in the form of a dental tray, having two or more walls that define a trough therebetween. Alternatively, the barrier layer may be in the form of a tray-like device having two or more walls, at least one of which includes cuts or discontinuities that help a person shape the barrier layer over the person's teeth and/or gums during installation. Where one or more of the walls includes deep cuts or discontinuities that yield one or more discontiguous walls, the tray-like treatment device may no longer have a trough.

The barrier layer may assume a particular shape prior to use independent of the treatment composition, or it may be so thin and flexible as to only be capable of assuming a shape as a result of the presence of an oral treatment composition and/or auxiliary adhesive composition adjacent to the barrier layer. In either case, the treatment and/or auxiliary adhesive composition acts as an endoskeleton that helps maintain the barrier layer in the shape of a dental tray or tray-like configuration prior to use. In this way, the treatment and/or adhesive composition helps keep the walls from spreading apart and/or collapsing together. In use, the barrier layer is reliably held in place over a user's teeth for a desired period of time by the adhesive action of the treatment and/or auxiliary adhesive composition.

The oral treatment and/or auxiliary adhesive composition may comprise a bead or a continuous layer substantially covering an inner surface of the barrier layer. The treatment and/or adhesive composition may be in the form of a sticky, viscous gel, it may be a stiff putty, or it may be solid or substantially solid. Sticky, viscous treatment gels can act as a highly viscous glue or adhesive that helps reliably maintain both the treatment and/or adhesive composition and barrier layer against the person's tooth and/or gum surfaces to be treated. Stiff putty, solid or substantially solid treatment compositions are typically dry or drier to the touch than gel compositions and can become more adhesive to teeth and/or gums when moistened with saliva or water during use.

Oral treatment compositions according to the invention generally comprise an active agent of some kind, a tissue adhesion agent, a liquid or gel solvent or carrier, and other active agents, inert ingredients or adjuvents as desired. Auxiliary adhesive compositions may optionally exclude one or more active agents contained in the oral treatment composition. Whether the treatment or adhesive composition is in the form of a sticky, viscous gel, a stiff putty, or a solid largely depends on the relative concentrations of the tissue adhesion agent and the solvent or carrier. Increasing the ratio of solvent or carrier relative to the tissue adhesion agent generally decreases the viscosity of the composition, while decreasing the ratio of solvent or carrier relative to the tissue adhesion agent yields a bleaching composition having a greater viscosity. Decreasing the concentration of the solvent or carrier at some point yields a composition that is so viscous as to be considered to be a putty, or even a solid. In one embodiment, a stiff yet plastically deformable putty is manufactured by first forming a treatment gel having a substantial quantity of a solvent and then removing a substantial portion of the solvent by evaporation to yield the putty composition. In another embodiment, a solid composition is made by removing additional solvent. Some residual water or solvent may still remain in the putty-like solid compositions after evaporation.

The size and shape of oral treatment devices according to the invention can be tailored to more readily fit a person's upper or lower dental arch. They may also be tailored to fit persons having differently-sized or shaped dental arches. The treatment devices are advantageously flexible and adhesive so as to readily conform to a wide variety of differently-sized teeth and dental arches. In one embodiment, the treatment devices are designed so as to substantially cover the front and lingual surfaces of the teeth and/or gums to be treated. Treating both surfaces helps penetration of the treatment composition into interproximal spaces between adjacent teeth.

The oral treatment devices according to the invention can be designed to be worn for any desired time period. In general, increasing the concentration of active agent within the treatment composition reduces the time required to effect a desired treatment. Nevertheless, due to the comfortable fit and reliable adhesion between the inventive treatment devices and the person's teeth, it is possible to wear such devices for extended periods of time to ensure even and thorough treatment. Treatment devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive treatment devices such as large, bulky bleaching dental appliances.

The oral treatment devices can be designed to be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional or overnight treatment while a person is sleeping, may last from about 2 hours to about 12 hours. Treatment sessions may be repeated as many times as are needed to obtain a desired degree of treatment. A typical treatment regimen will preferably include 1–20 treatment sessions, more preferably 2–15 treatment sessions, and most preferably 3–10 treatment sessions.

For convenience of use, multiple oral treatment devices may be packaged together and sold as a kit. In one embodiment, the number of oral treatment devices provided with each kit can equal the number of sessions that represent a prescribed treatment regimen. To efficiently utilize the space within a kit package, multiple treatment devices can be stacked, internested, or laid together within a package. The treatment devices can be sealed collectively or individually as desired. They may contain a removable protective layer on their interior surfaces to protect the bleaching composition from contamination or moisture.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1A:
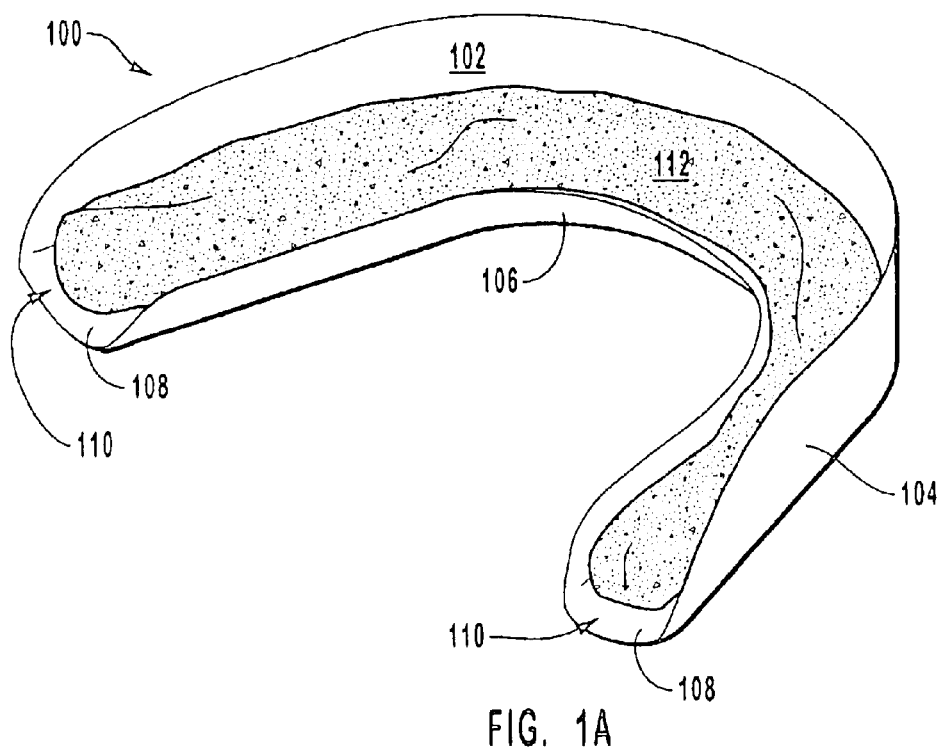
FIG. 1A is a perspective view of an exemplary oral treatment device according to the invention comprising a barrier layer in the shape of a dental tray having a trough and an oral treatment or adhesive composition within the trough in the form of a bead that at least partially assists in maintaining the barrier layer in the shape of a tray.

The present invention relates to improved oral treatment devices used to treat a person's teeth and/or gums. The inventive treatment devices include a thin, flexible barrier layer and an endoskeleton comprising an oral treatment composition and/or an auxiliary adhesive composition. The barrier layer protects the treatment composition and adhesive composition from saliva or moisture within a person's mouth during use, which keeps them in contact with the person's teeth and/or surrounding soft tissue and helps prevent or minimize their diffusion into the user's oral cavity.

The inventive treatment devices are more adhesive to teeth and/or gums than conventional dental bleaching strips and are less intrusive than bulky, over-the-counter, non-custom or boil-and-bite dental trays. In some cases they may be as reliable as, or even more reliable than, custom-fitted dental trays in maintaining a treatment composition against a person's teeth and/or gums. To some people they may be at least as comfortable as custom-fitted trays.

The term "barrier layer", as used herein, refers to one or more layers of a material that protects the treatment composition and optional adhesive composition from ambient moisture and saliva found within a person's mouth when the treatment device is placed over the person's teeth. The barrier layer may also serve to protect the treatment and/or adhesive compositions from moisture and contaminants during storage and prior to use. The barrier layer may be able to maintain itself in a desired shape independent of an adjacent endoskeleton composition, or it may be so thin and flexible as to have no predetermined shape absent the existence of the endoskeleton.

The term "endoskeleton" refers to any oral treatment composition and/or auxiliary adhesive composition that, when positioned adjacent to the barrier layer, helps maintain the barrier layer in the form of a dental tray or tray-like configuration prior to use. In cases where the barrier layer at least partially conforms to the shape of a dental tray or has a tray-like configuration independent of the endoskeleton, the endoskeleton will provide additional support in order to help maintain the barrier layer in the shape of a dental tray or tray-like configuration prior to use. In the case where the barrier layer has no predetermined shape, the endoskeleton will determine and maintain the shape of the barrier layer prior to use. The "endoskeleton" may have a consistency ranging from a sticky, viscous gel to a solid composition.

The term "sticky, viscous gel" shall refer to treatment and/or auxiliary adhesive compositions that have been formulated or processed so that they do not readily flow by the force of gravity but are viscous so that they can be expressed from a syringe orifice or other dispensing means known in the art.

At some point, when the viscosity of a highly viscous gel becomes so great as to yield a composition that is substantially solid but still plastically deformable, it may be considered to be a "stiff putty". The difference between a "sticky, viscous gel" and a "stiff putty" is a matter of degree. Likewise, a "stiff putty" can become so stiff or rigid as to become a "solid".

The term "substantially solid", as used herein, refers to a treatment composition or auxiliary adhesive composition that is in a solid or semi-solid condition. In one aspect, a "substantially solid" composition can be characterized as a cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of a treatment or adhesive composition, also excludes dry particulate compositions or powders because dry particulates and powders readily flow when subjected to gravity and/or are readily separated (i.e., the particles as a whole have little or no internal cohesion). Moreover, powders or particulates, when viewed as a whole, are not coherent or solid.

In one embodiment, "stiff putty" and the "substantially solid" compositions become more adhesive when moistened with saliva or water. When moistened, the surface of the substantially solid or putty composition turns into a sticky material that is able to more strongly adhere to teeth compared to a substantially solid or putty composition that has not been moistened. The substantially solid or putty composition may, at least on the surface, become a viscous liquid, paste or gel, at least temporarily, depending on the amount of moisture that is applied to the surface of the "substantially solid" or putty-like composition. The consistency of the moistened surface can remain "substantially solid" or putty-like depending on the degree of initial moistening, or it can stiffen and even revert back to being "substantially solid" or putty-like as the initial quantity of surface moisture diffuses into a remaining portion of the "substantially solid" or putty-like composition over time (e.g., during an oral treatment procedure in which the composition is protected from saliva and ambient moisture in a person's mouth by a moisture-resistant barrier layer).

The term "dental tray", as used herein, refers to an appliance having a tray-like shape so as to facilitate placement of the device over at least a portion of a person's dental arch. In one embodiment, a "dental tray" includes a front side wall configured to engage front surfaces of a person's teeth when in use, a rear side wall extending laterally from the front side wall, either abruptly by one or more distinct angles or non-abruptly by a curved transition portion, configured to engage lingual surfaces of the person's teeth, and a trough between said front and rear side walls. A "dental tray" may be configured so that a portion of the front side wall, rear side wall, or a transition portion thereof (e.g., a bottom wall), engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever contiguous front and rear side walls have a space therebetween and are laterally offset by an angle of less than 180°. In practice, the front and rear side walls will be offset by an angle that is preferably less than about 150°, more preferably less than about 120°, and most preferably less than about 90°.

In the case where the front and rear side walls are connected by a transition portion (e.g., a trough having a U-shaped or rectangular cross section), at least a portion of the front and rear side walls may be substantially parallel (i.e., be offset by an angle of approximately 0°) or offset by a very small angle. In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls may be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when referring to a dental tray or treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

In the case where the treatment device includes one or more walls containing cuts or other discontinuities so that the wall is not contiguous, there may be sufficient space or spaces between the individual flaps or segments making up the discontiguous wall so that a "trough" no longer exists between the front and bottom sidewalls or flaps. Thus, the term "trough" should be understood as the region between two or more contiguous walls that define an inner region that can hold or contain a liquid or gel therewithin. Where one of the walls is significantly discontiguous so as to yield a device that allows a liquid to pour through or out of the cuts or discontinuities, the space or region between the sidewalls is not a "trough" but is simply an interior region between the walls.

The term "molecular weight", as used herein, shall refer to number average molecular weight expressed in Daltons, unless otherwise specified.

II. Oral Treatment Devices

Oral treatment devices according to the invention include a thin, flexible barrier layer that protects a treatment composition, and optionally an auxiliary adhesive composition, from ambient moisture within a person's mouth during use. The treatment and/or adhesive compositions act as an endoskeleton so as to at least partially maintain the barrier in a desired shape of a try or tray-like configuration prior to use. The treatment and/or adhesive compositions can range from a sticky, viscous gel to a solid composition that becomes more adhesive when moistened with saliva or water. Following are preferred examples of barrier layers, treatment compositions, and auxiliary adhesive compositions according to the invention, as well as characteristics of treatment devices made therefrom.

A. Barrier Layers

The barrier layer is preferably moisture-resistant in order to protect the treatment and/or auxiliary adhesive compositions from ambient moisture found in a person's mouth. According to one embodiment, the barrier layer comprises a thin, flexible membrane formed from a moisture-resistant polymer material. Thin, flexible barrier layers preferably have a thickness in a range of about 0.0001 inch to about 0.012 inch, more preferably in a range of about 0.001 inch to about 0.01 inch. The barrier layers may be capable of forming a dental tray or tray-like device absent an endoskeleton, or they may be shapeless requiring an endoskeleton.

Examples of materials that can be used to form the barrier layer include, but are not limited to, polyolefins, wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Examples of suitable polyolefins that can be uses to make the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The barrier layer may comprise a polymeric blend and/or multiple layers comprising two or more of the foregoing materials. Plasticizers, flow additives, and fillers known in the art can be used as desired to modify the properties of any of the foregoing polymers used to form the barrier layer.

According to one embodiment, the barrier layer is formed of a mixture of ethylene-vinyl acetate copolymer (EVA) and polypropylene (PP), preferably comprising about 5% to about 35% PP, more preferably about 10% to about 30% PP, more especially preferably about 15% to about 25% PP, and most preferably about 20% PP, with the balance comprising ethylene-vinyl acetate (EVA), and optionally other polymers and/or small quantities of additives such as plasticizers.

Other materials that can act as a barrier layer include cellulosic ethers, cellulose acetate, polyvinyl acetate, polyvinyl alcohol, shellac, and chemical or light-cure materials (e.g., methacrylate or acrylate resins). Examples of useful cellulosic ethers that can be used to form a barrier layer include, but are not limited to, ethyl cellulose, propyl cellulose, isopropyl cellulose, butyl cellulose, t-butyl cellulose, and the like.

B. Oral Treatment Compositions

Oral treatment compositions according to the invention may have a consistency ranging from a sticky, viscous gel to a solid. Substantially solid or putty compositions preferably become more sticky and adhesive to teeth and/or gums when moistened with water or saliva. The treatment compositions may comprise a bead or a continuous layer positioned so as to cover one or more of a person's tooth surfaces and/or gums. The treatment composition can be positioned directly adjacent to the barrier layer, or at least a portion of the treatment composition may be positioned adjacent to an auxiliary adhesive composition.

In general, sticky, viscous treatment gels will include at least one active agent, at least one tissue adhesion (or thickening) agent, a liquid or gel, solvent, carrier or vehicle into which the active agent and tissue adhesion agent are dispersed, and other components and adjuvents as desired. The main difference between compositions that are a "gel" and those that are a "putty" or a "solid" is the level of solvent or carrier within the composition. In general, the greater the concentration of solvent or carrier relative to the tissue adhesive agent, the more gel-like is the composition. The lower the concentration of solvent or carrier relative to the tissue adhesion agent, the more putty-like or solid is the composition. At some point, the ratio of solvent or carrier to tissue adhesion agent is low enough for a gel composition to transition into being a stiff or highly viscous putty, or for a putty to transition into a solid.

Stiff putties and solids preferably become more adhesive to teeth when moistened with water or saliva. Solid or putty compositions can have so little solvent or carrier so as to feel dry to the touch and be initially non-adhesive but that become more adhesive to teeth and/or gums when moistened with water or saliva. Substantially solid or putty compositions can be made by initially including a very small amount of solvent or carrier and/or by first forming a gel that is later dried to remove a substantial portion of the solvent or carrier.

Following are exemplary active agents, tissue adhesion agents, solvents or carriers, and other components that may be used to manufacture oral treatment compositions according to the invention.

1. Active Agents

Examples of active agents that can be used within oral treatment compositions according to the invention include dental bleaching agents, desensitizing agents, remineralizing agents, antimicrobial agents, anti-plaque agents, anti-tartar agents, gingival soothing agents, anesthetics, anti-oxidants, and mouth freshening agents. Examples of dental bleaching agents include, but are not limited to, aqueous hydrogen peroxide, carbamide peroxide, metal perborates (e.g., sodium perborate), metal percarbonates (e.g., sodium percarbonate), metal peroxides (e.g., calcium peroxide), metal chlorites and hypochlorites, peroxy acids (e.g., peroxyacetic acid), and peroxy acid salts.

Bleaching agents within dental bleaching compositions according to the invention can have any desired concentration, e.g., between 1–90% by weight of the dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period. One or more bleaching agents are preferably included in an amount in a range of about 1% to about 60% by weight of the dental bleaching composition, more preferably in a range of about 5% to about 40% by weight, and most preferably in a range of about 10% to about 30% by weight.

Examples of other active agents that may be included in addition to, or instead of, the dental bleaching agent include desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents and preservatives (e.g., chlorhexidine, triclosan, sodium benzoate, parabens, tetracycline, phenols, and cetyl pyridinium chloride), anti-plaque agents, anti-tartar agents (e.g., pyrophosphates), gingival soothing agents (e.g., aloe vera, mild potassium nitrate, isotonic solution-forming salts), anesthetics (e.g., benzocaine, lidocain, and the like), anti-oxidants (e.g., vitamin A, vitamin C, vitamin E, other vitamins, and carotene), and mouth freshening agents (e.g., camphor and wintergreen).

2. Tissue Adhesion Agents

Useful tissue adhesion agents (or tackifying agents) include a wide variety of hydrophilic polymers. Examples of hydrophilic polymer tissue adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like.

Non-limiting examples of polyvinyl pyrrolidone polymers that have been used in formulating oral treatment compositions according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the oral treatment composition is a gel, the one or more tissue adhesion agents are preferably included in an amount in a range of about 1% to about 50% by weight of the treatment gel, more preferably in a range of about 3% to about 30% by weight, and most preferably in a range of about 5% to about 20% by weight.

In the case where the oral treatment composition is substantially solid, the one or more tissue adhesion agents are preferably included in an amount in a range of about 10% to about 90% by weight of the substantially solid treatment composition, more preferably in a range of about 20% to about 80% by weight, and most preferably in a range of about 40% to about 75% by weight.

3. Carriers and Vehicles

Sticky, viscous oral treatment gels will typically include one or more liquid or gel, solvents, carriers or vehicles into which the active agent, tissue adhesion agent, and other components are dissolved or dispersed. Examples of liquid or gel solvents, carriers or vehicles include, but are not limited to, water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

In the case of compositions that are substantially solid or a stiff putty, the concentration of solvent, carrier or vehicle will typically be attenuated compared to treatment gels. Where it is desired to form a treatment gel that is later converted into a putty or solid composition, it may be advantageous to include one or more volatile solvents that can be removed by evaporation (e.g., water, alcohols, acetone, and other organic solvents). Because of the affinity of hydrophilic polymers for water, even treatment compositions that appear to be solid may include a significant amount of bound water (e.g., up to about 10% or more by weight of the treatment composition). In the case where the treatment composition has the consistency of a highly viscous or stiff putty, the composition will generally include a solvent, carrier or vehicle that acts as a plasticizer or softening agent.

4. Other Components

The oral treatment compositions may optionally include other components as desired to yield treatment compositions having desired properties. Examples include bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal polyphosphates, and alkyl sulfates), neutralizing agents (e.g., sodium hydroxide and triethanolamine), inorganic thickening agents (e.g., fumed silica), colorants, flavorants, sweeteners, and the like.

C. Auxiliary Adhesive Compositions

Auxiliary adhesive compositions, when optionally used in manufacturing oral treatment devices according to the invention, may include no active agents, or they may include significantly less active agent, or a different active agent, compared to the oral treatment composition. Aside from that, they may include any of the components set forth above with respect to the oral treatment composition. The auxiliary adhesive composition may be positioned between the treatment composition and barrier layer. Or it may be positioned adjacent to or surround the treatment composition, e.g., so as to shield a person's gums or periodontal tissue from a bleaching composition during use, thereby confining the bleaching agent to an area adjacent to the person's tooth surfaces to be bleached.

Like the treatment composition, the auxiliary adhesive composition can range from a sticky, viscous gel to a solid. It can be a bead or layer. The adhesive composition can be positioned in a limited region near the rim(s) or edge(s) of the barrier layer nearest the person's gums when the treatment device is in use, or a portion may extend beneath the treatment composition. Alternatively, a bead of the adhesive composition may be positioned on top of a portion of the treatment composition.

In general, auxiliary adhesive compositions will include at least one tissue adhesion (or tackifying) agent and a liquid or gel solvent, carrier or vehicle into which the tissue adhesion agent is dispersed, at least in the case of a gel and/or during the manufacture of a substantially solid adhesive composition. The tissue adhesion agent preferably comprises a hydrophilic polymer (e.g., one or more of the hydrophilic polymers discussed above with respect to the dental bleaching composition). The relative amount of tissue adhesion agent to liquid solvent, carrier or vehicle can be varied to yield either a sticky, viscous gel or a solid adhesive composition, as discussed above. The solvent, carrier or vehicle may comprise any of the solvents, carriers or vehicles discussed above with respect to the bleaching composition.

The auxiliary adhesive composition may include other components as desired, including colorants (e.g., carotene), gingival soothing agents (e.g., aloe vera, mild potassium nitrate, isotonic solution-forming salts (e.g., sodium chloride in an amount of about 0.9% by weight), and anesthetics (e.g., benzocaine, lidocain and the like), antioxidants (e.g., vitamin A, vitamin C, vitamin E, other vitamins, chlorophyll and carotene), flavoring agents, antimicrobial agents and preservatives (e.g., sodium benzoate, parabens, triclosan, phenols, chlorhexidine, and cetylpyridinium chloride), mouth freshening agents (e.g., camphor and wintergreen), bleaching agent stabilizers (e.g., EDTA, citric acid and sodium lauryl sulfate), inorganic thickening agents (e.g., fumed silica and fumed aluminum oxide), remineralizing agents (e.g., sodium fluoride or other fluoride salts), anti-plaque agents, anti-tartar agents, bleaching agent activators, and other adjuvents as desired.

D. Characteristics of Oral Treatment Devices

Figure 1B:
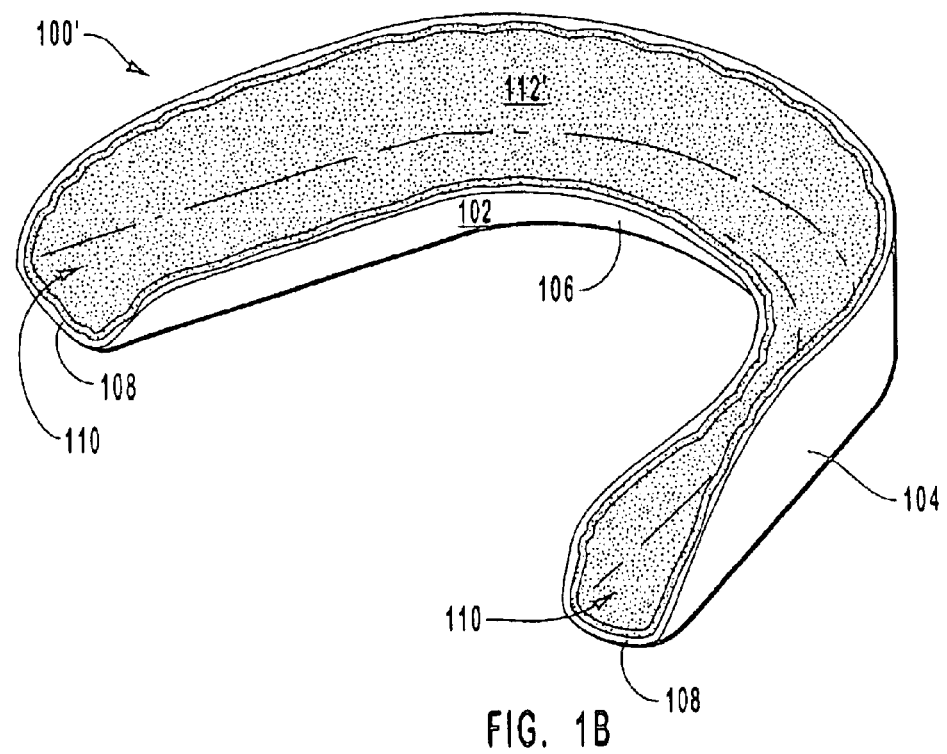
FIG. 1B is a perspective view of an exemplary oral treatment device according to the invention comprising a barrier layer in the shape of a dental tray having a trough and an oral treatment composition within the trough in the form of a continuous layer that at least partially assists in maintaining the barrier layer in the shape of a tray.

According to one embodiment, the oral treatment devices have a horseshoe shaped longitudinal profile and a trough with a U-shaped cross section, much like a conventional bleaching tray. Exemplary treatment devices in the form of a dental tray are depicted in FIGS. 1A and 1B. FIG. 1A is a perspective view of an oral treatment device 100 comprising a flexible barrier layer 102 having a front side wall 104, a rear side wall 106, and a horseshoe shaped bottom wall 108 that together define a trough 110 having a generally U-shaped cross section throughout the entire longitudinal dimension. Disposed within the trough 110 is a continuous bead of an oral treatment composition 112 that acts as an endoskeleton so as to at least partially maintain the barrier layer 102 in the form of a dental tray having a trough with a U-shaped cross section. The oral treatment composition 112 may have a consistency ranging from a sticky, viscous gel to a solid treatment composition. The bead of oral treatment composition 112 is preferably a sticky, viscous gel having a cross-sectional diameter or thickness in a range of about 1 mm to about 5 mm, more preferably in a range of about 2 mm to about 4 mm.

FIG. 1B depicts an oral treatment device 100' that includes a barrier layer 102 in the form of a dental tray having a substantially U-shaped cross section. The barrier layer 102 includes a front sidewall 104, a rear sidewall 106, and a horseshoe shaped bottom wall 108 that together define a trough 110 having a general U-shaped cross section throughout the entire longitudinal dimension. Disposed within the trough 110 is a continuous layer of an oral treatment composition 112'. The oral treatment composition 112' may range from a sticky, viscous gel to a solid composition. The continuous layer of treatment composition 112' is preferably a stiff putty or a solid composition having a thickness in a range of about 0.2 mm to about 2 mm, more preferably in a range of about 0.5 mm to about 1 mm.

Figure 2A:
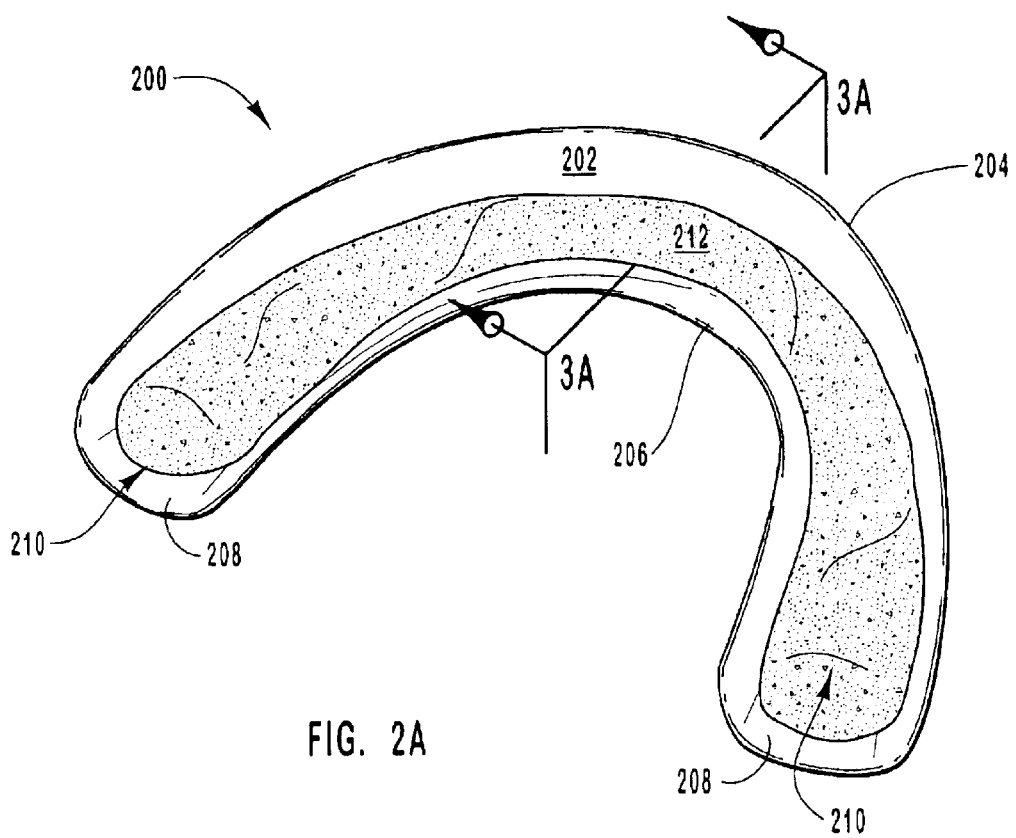
FIGS. 2A and 2B are perspective views of exemplary oral treatment devices according to the invention comprising a barrier layer in the shape of a dental tray having a trough and a dental treatment composition within the trough in the form of a bead or continuous layer that at least partially assists in maintaining the barrier layer in the shape of a tray.
Figure 2B:
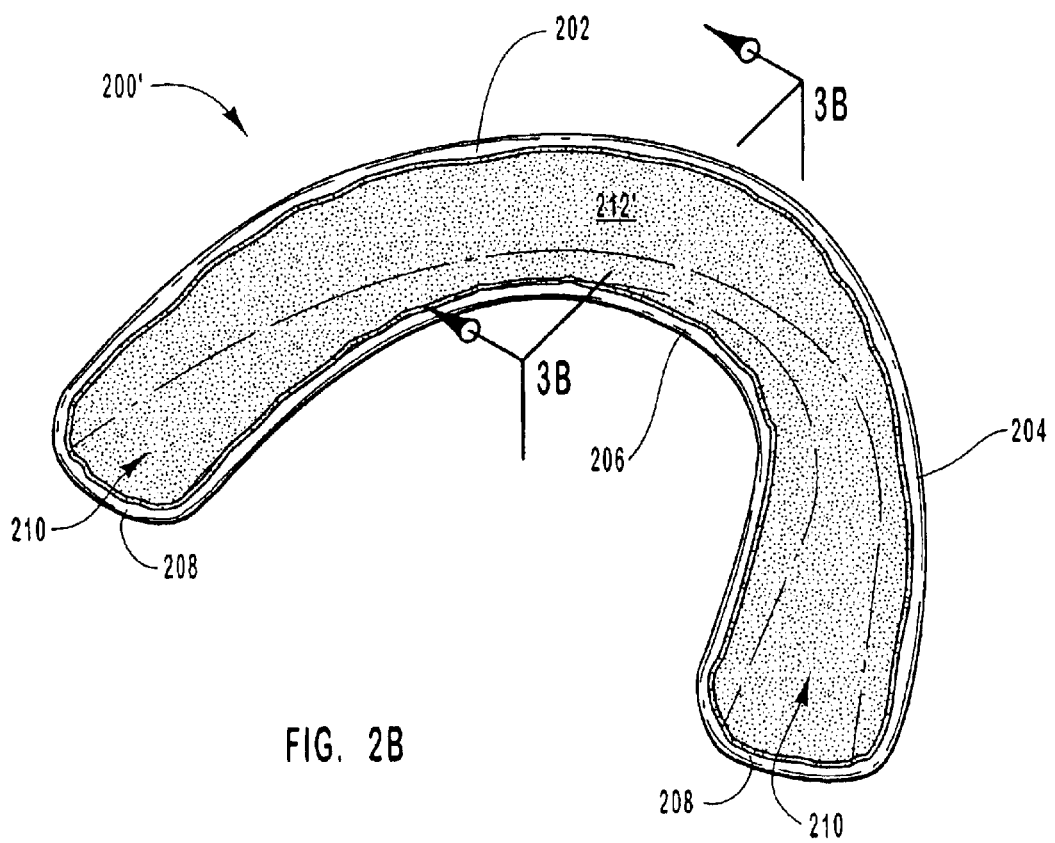
Figure 3A:
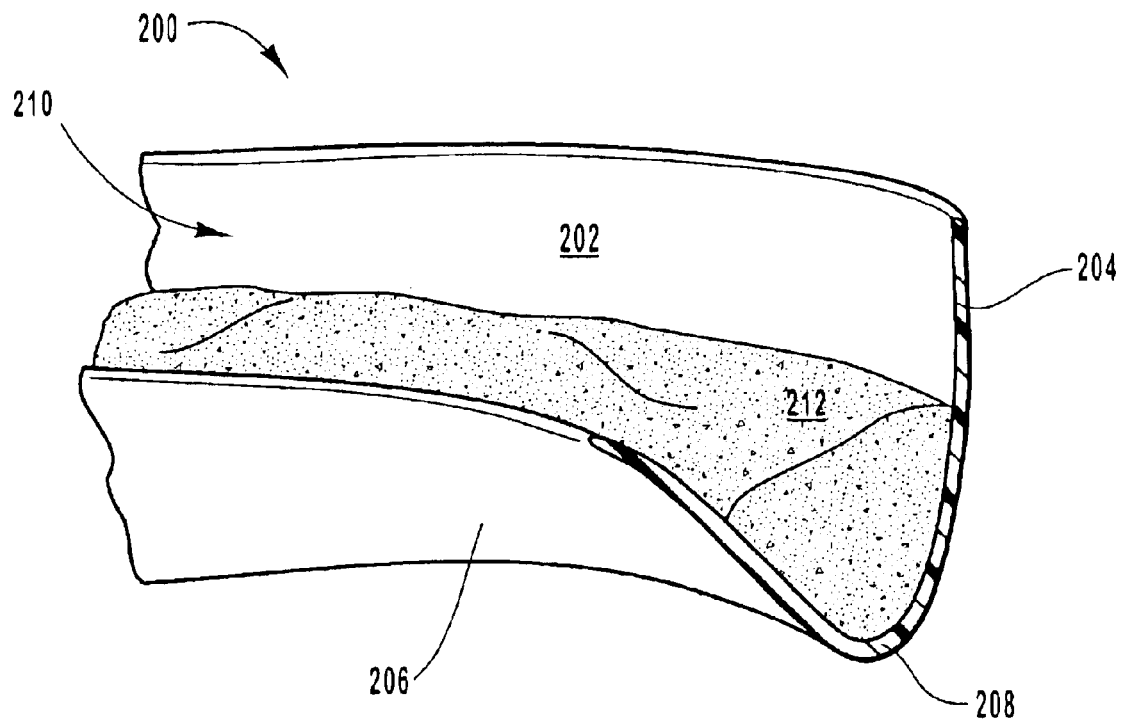
FIGS. 3A and 3B are cross-sectional views of the oral treatment devices of FIGS. 2A and 2B, respectively.
Figure 3B:
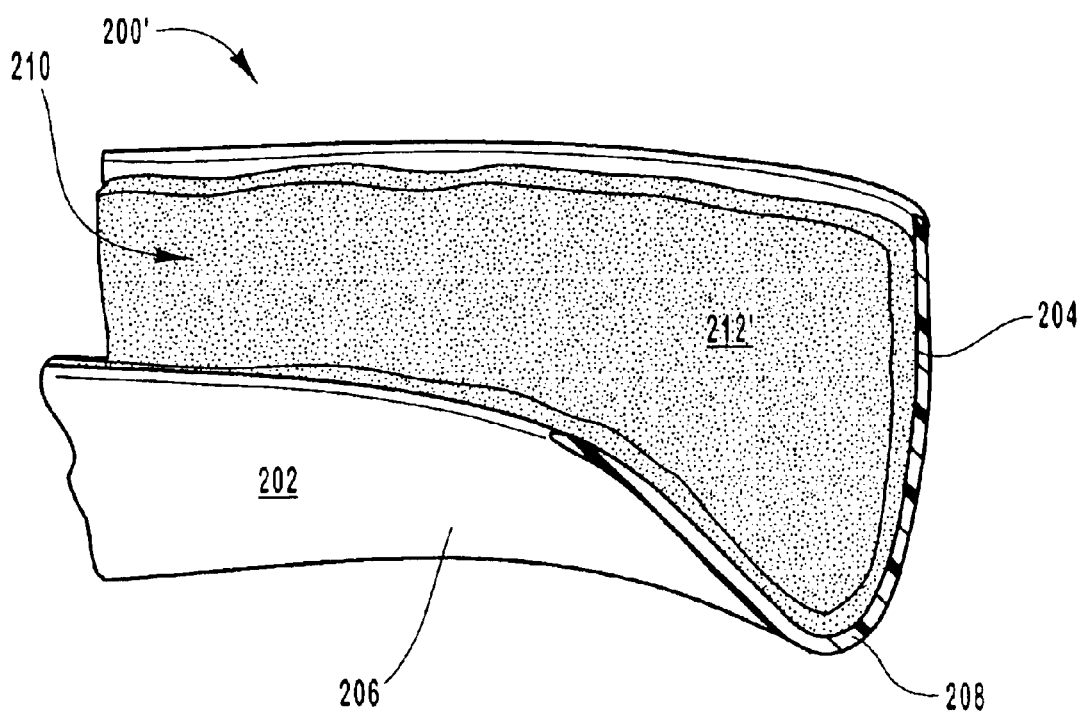

FIGS. 2A and 2B depict oral treatment devices 200 and 200' having a generally U-shaped trough, but that narrows so as to have more of a V-shaped cross section in the vicinity of the incisors, as shown more particularly in FIGS. 3A and 3B. As shown in FIGS. 2A and 3A, oral treatment device 200 includes a barrier layer 202 having a front sidewall 204, a rear sidewall 206, and a bottom wall 208 that together define a trough 210. A continuous bead of an oral treatment composition 212 is positioned within the trough 210, and is formulated so as to act as an endoskeleton that at least partially helps maintain the barrier layer 202 in the shape of a dental tray.

As shown in FIGS. 2B and 3B, an oral treatment device 200' includes a barrier layer 202 having a front sidewall 204, a rear sidewall 206, and a bottom wall 208 that together define a trough 210 having a substantially U-shaped cross section that narrows to a substantially V-shaped cross section in the vicinity of the incisors. A continuous layer of an oral treatment composition 212' is positioned within the trough 210 and is formulated so as to act as an endoskeleton that at least partially helps maintain the barrier layer 202 in the shape of a dental tray.

Figure 4A:
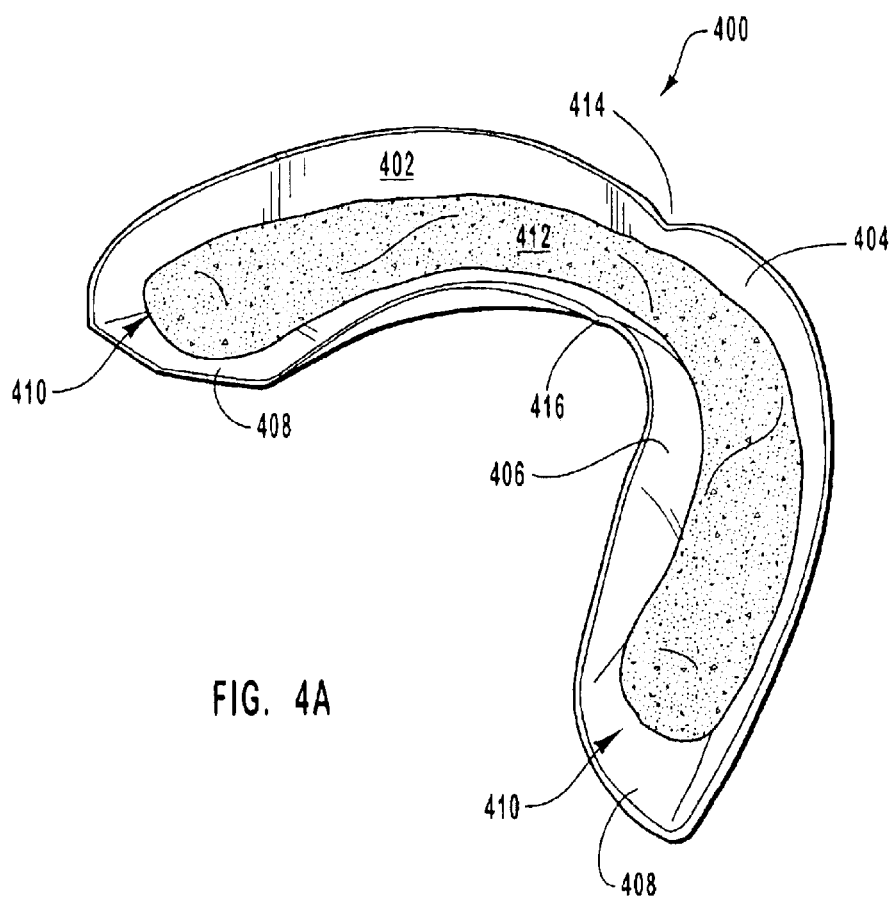
FIGS. 4A and 4B are perspective views of exemplary oral treatment devices according to the invention that include notches in the side walls that assist the treatment devices in conforming to variously sized and/or shaped dental arches.
Figure 4B:
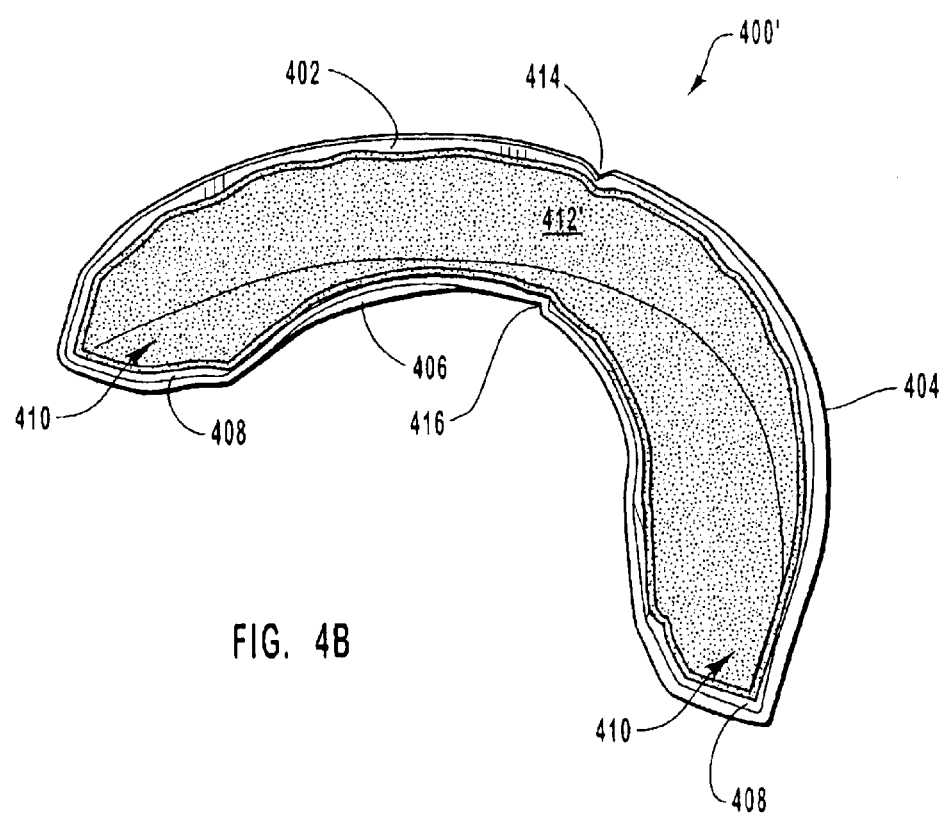

FIGS. 4A and 4B depict oral treatment devices 400 and 400', each of which include a barrier layer 402 having a front sidewall 404, a rear sidewall 406, and a bottom wall 408 that together define a trough 410 into which either a bead of treatment composition 412 (FIG. 4A) or a continuous layer of treatment composition 412' (FIG. 4B) is disposed. In addition, the oral treatment devices 400 and 400' include a first notch 414 in the front sidewall 404 and a second notch 416 in the rear sidewall 406. The notches 414 and assist the oral treatment devices 400 and 400' in conforming to variously sized and shaped dental arches.

Figure 5A:
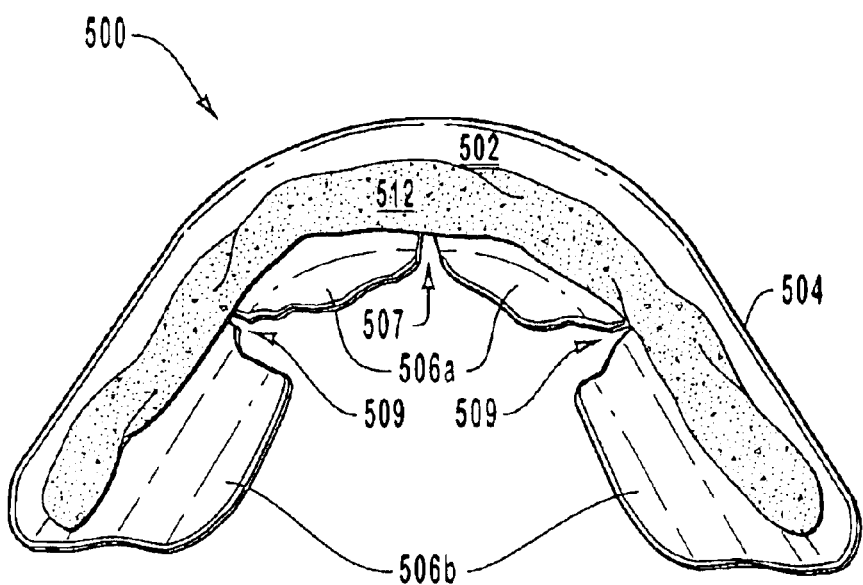
FIGS. 5A and 5B are perspective views of exemplary oral treatment devices according to the invention comprising a barrier layer having a tray-like configuration with cuts or discontinuities in a bottom wall so as to yield a device having no trough, and a treatment or adhesive composition in the form of a bead or continuous layer adjacent to the barrier layer.
Figure 5B:
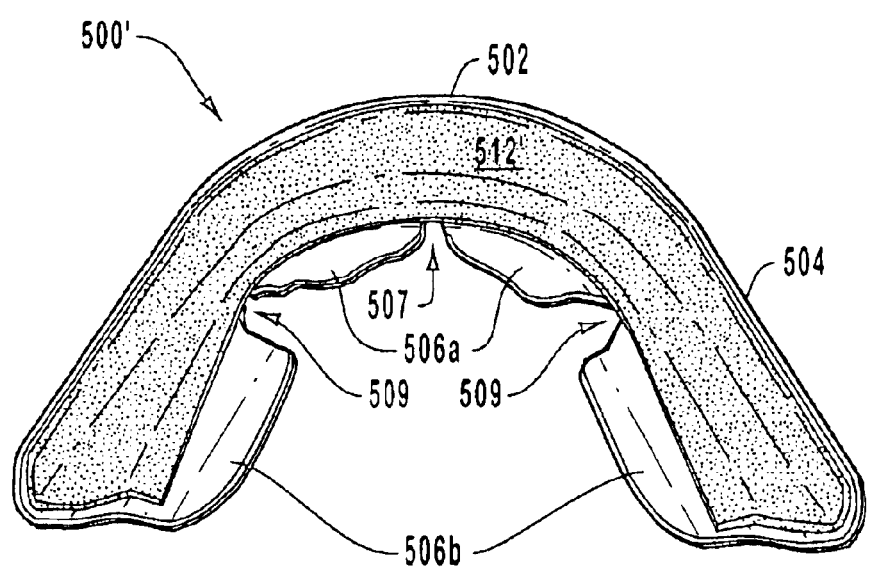

The FIGS. 5A and 5B depict oral treatment devices 500 and 500' that are configured so as to have a noncontiguous bottom or rear wall. In this way, the oral treatment devices 500 and 500' include no "trough" as that term is ordinarily understood in the context of conventional dental trays having contiguous walls that join together so as to define a trough.

Instead of contiguous sidewalls, each of oral treatment devices 500 and 500' includes a barrier layer 502 having a front sidewall 504, first bottom flaps 506a separated by a first cut or discontinuity 507, and second bottom flaps 506b separated from the first bottom flaps 506a by second cuts or discontinuities 509. The first bottom flaps 506a are sized and configured so as to wrap around and lie adjacent to the inner surfaces of a person's incisors and canines when in use. Second bottom flaps 506d are sized and configured so as to wrap around and contact inner surfaces of a person's bicuspids and optionally one or more molars.

The cuts or discontinuities 509 between first flaps 506a and second flaps 506b facilitate good adhesion of the first bottom flaps 506a to a person's incisors and canines, particularly at the junction of the canines and bicuspids. The cuts or discontinuities 509 compensate for the abrupt difference in width between a person's bicuspids adjacent to the second bottom flaps 506b and the canines adjacent to the first bottom flaps 506a. The discontinuity or cut 507 separating first bottom flaps 506a from each other further assists in conforming the flaps 506a to the inner surfaces of a person's incisors and canines.

FIG. 5A further shows a continuous bead of an oral treatment composition 512 disposed within an interior region defined by front sidewall 504 and bottom flaps 506a and 506b. FIG. 5B alternatively depicts a substantially continuous layer of an oral treatment composition 512' disposed within an interior region defined by the front sidewall 504 and bottom flaps 506a and 506b.

Figure 6A:
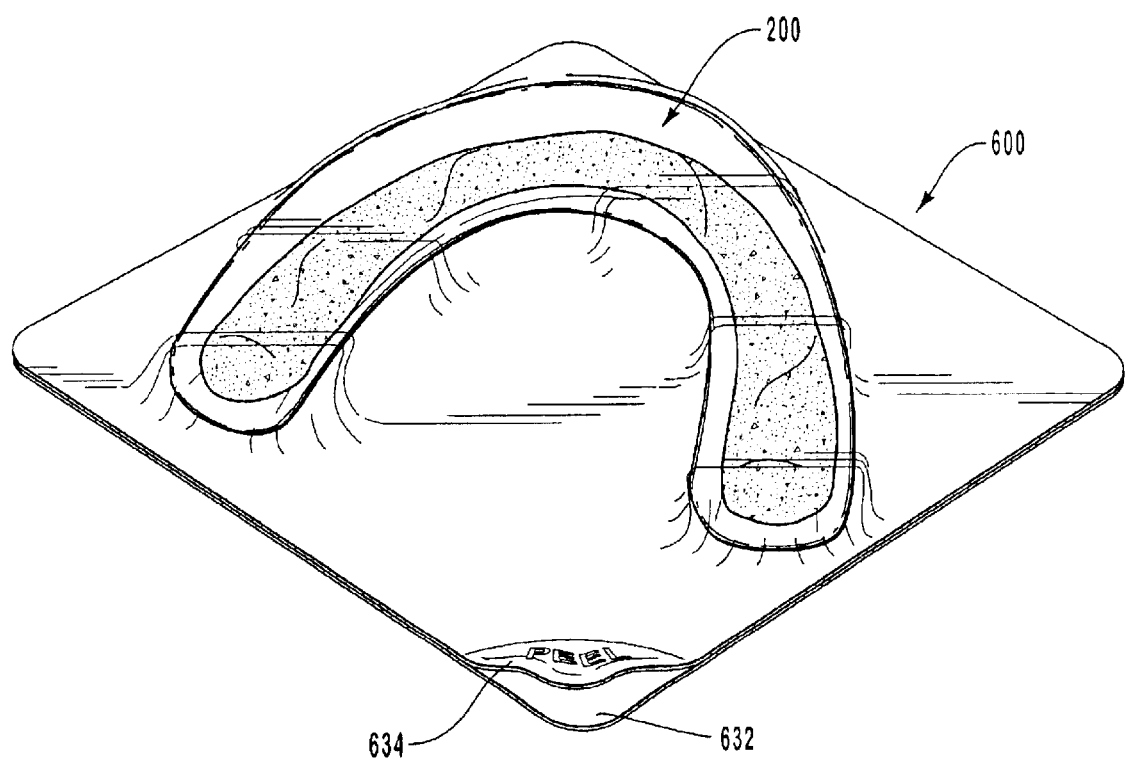
FIGS. 6A and 6B illustrate the oral treatment devices of FIGS. 2A and 2B, respectively, contained within sealed protective packages having a peelable cover.
Figure 6B:
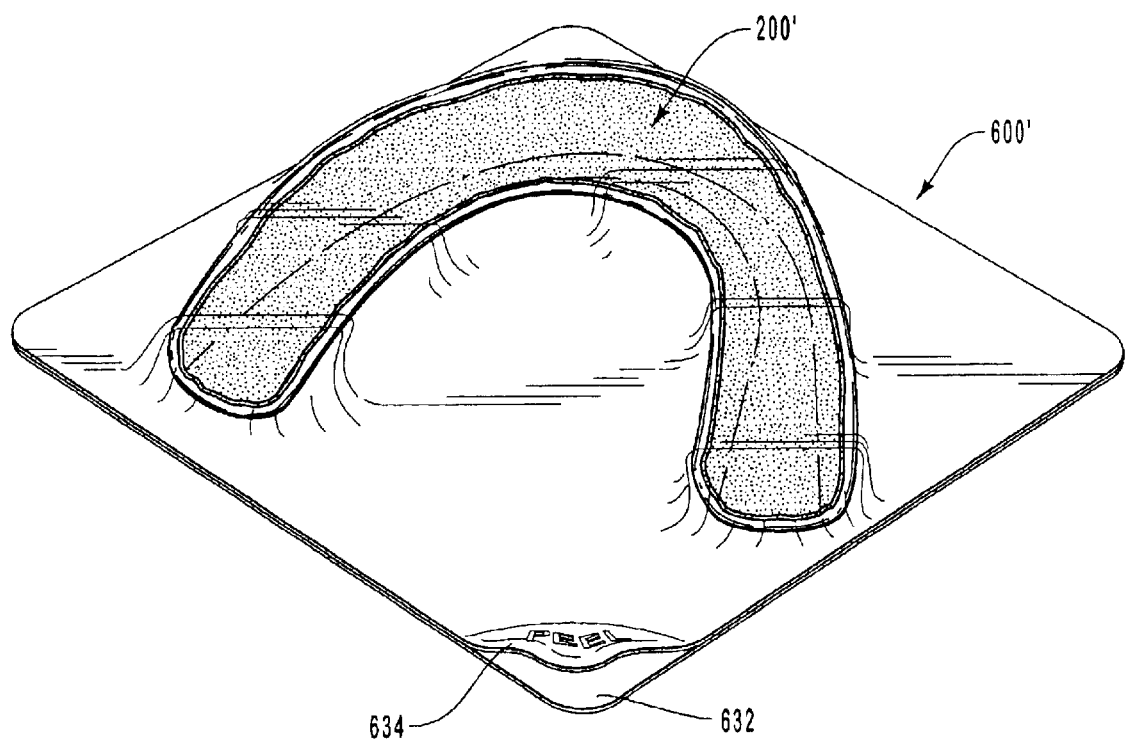

In order to protect oral treatment devices according to the invention from contaminants during storage and prior to use, the treatment devices can be packaged within a sealed container or package. As illustrated in FIGS. 6A and 6B, exemplary oral treatment devices 200 and 200' can be sealed within a protective package 600 or 600' that includes a rigid support layer 632 and a peelable cover 634. When it is desired to use the oral treatment device 200 or 200', the peelable cover 634 is removed and the treatment device 200 or 200' is removed or separated from the support layer 632.

In one embodiment, the support layer 632 includes a shaped portion that can act as an exoskeleton to further assist in maintaining the treatment device 200 or 200' in the shape of a dental tray prior to use. In use, both the treatment device 200 or 200' and support layer 632 can be placed into a person's mouth so as to initially position the treatment device 200 or 200' over the person's teeth and/or gums. Thereafter, the support layer 632 is removed, leaving only the treatment device 200 or 200' within the person's mouth. This permits further manipulation of the barrier layer 202 in order for the treatment device 200 or 200' to better conform to the shape and irregularities of the person's teeth.

In addition to, or instead of, a protective package, the treatment device may alternatively include a removable protective layer (not shown) that is temporarily placed within the trough or interior region adjacent to the treatment composition and/or auxiliary adhesive composition. When it is desired to use the treatment device, the removable protective layer is removed so as to expose the treatment composition and/or auxiliary adhesive composition.

Figure 7A:
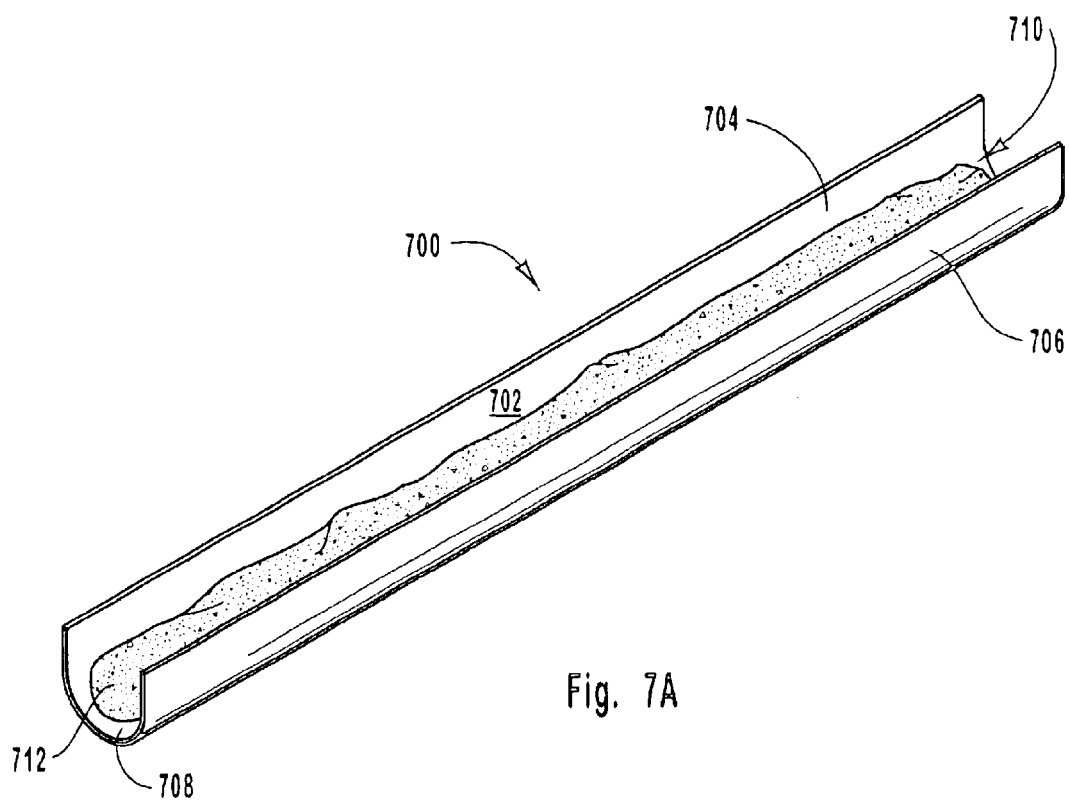
FIGS. 7A and 7B are perspective views of exemplary oral treatment devices having a barrier layer in the form of a U-shaped trough and a bead or continuous layer of a treatment or adhesive composition within the trough.
Figure 7B:
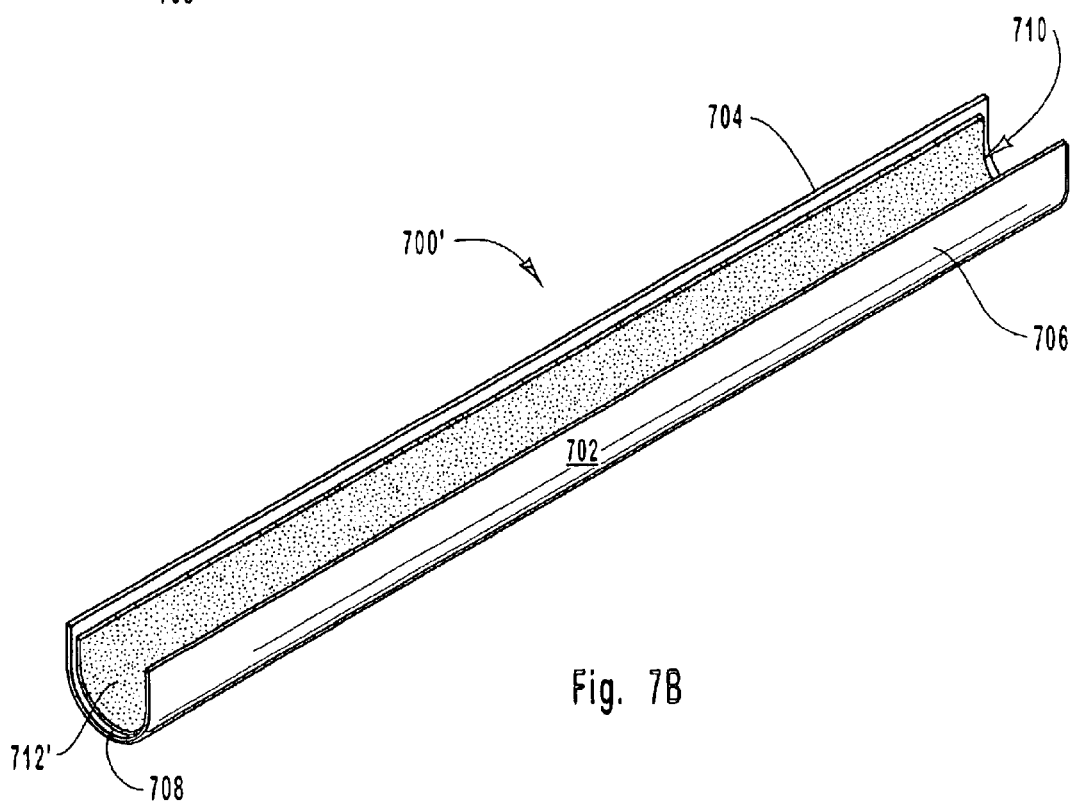

FIGS. 7A and 7B depict an alternative embodiment of an oral treatment device 700 or 700'0 having a U-shaped trough but a substantially linear or straight longitudinal profile. More particularly, the oral treatment devices 700 and 700' include a barrier layer 702 having a front sidewall 704, a rear sidewall 706, and a bottom sidewall 708 that together define a U-shaped trough 710 into which a bead of an oral treatment composition 712 or a continuous layer of a treatment composition 712' is disposed.

Figure 8A:
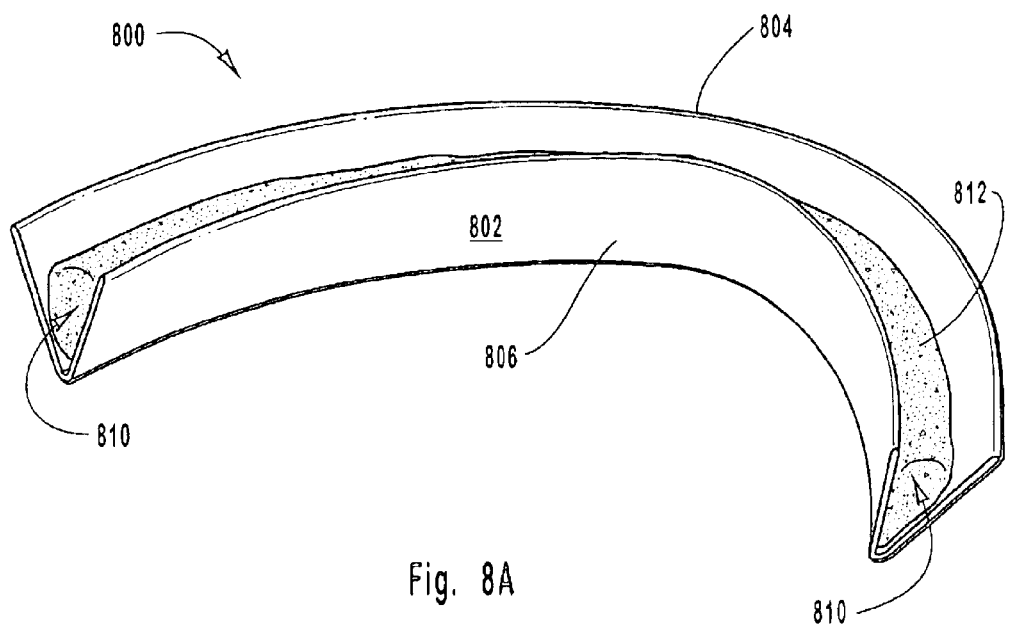
FIGS. 8A and 8B are perspective views of exemplary oral treatment devices having a barrier layer in the form of a V-shaped trough and a treatment or adhesive composition in the form of a bead or continuous layer within the trough.
Figure 8B:
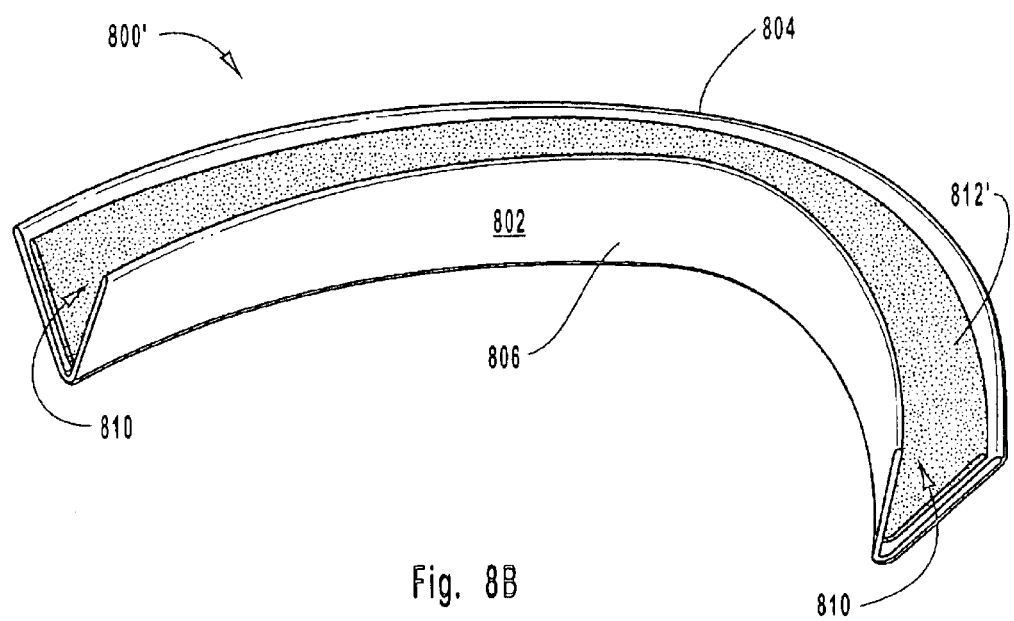

FIGS. 8A and 8D depict another alternative embodiment of an oral treatment device 800 or 800' having a V-shaped trough. More particularly, the oral treatment devices 800 and 800" include a barrier layer 802 having a front sidewall 804 and a rear sidewall 806 that together define a V-shaped trough 810 within which a bead of an oral composition 812 or a layer of an oral composition 812' is disposed.

III. Methods of Making Oral Treatment Devices

The various components that make up the inventive oral treatment devices according to the invention can be assembled or brought together in any desired order. In the case where the barrier layer is able to maintain its shape as a dental tray or tray-like configuration, the oral treatment composition and optional auxiliary adhesive composition can simply be placed within the trough or interior region of the dental tray or tray-like device. Thereafter, the oral treatment device can be further manipulated, modified, or packaged as desired to yield the desired oral treatment device In the case where the barrier layer is so thin and flexible so as to be incapable of maintaining itself in a desired configuration independent of an endoskeleton composition, various options exist. In the case where the oral treatment composition and/or auxiliary adhesive composition are sticky, viscous gels, it may be advantageous to place the barrier layer inside of an exoskeleton or template in order to form a dental tray or a device having a tray-like configuration. Thereafter, the gel composition can act as an endoskeleton so it can maintain the barrier layer in the form of a tray or tray-like configuration in the absence of the external support or exoskeleton.

In another embodiment, the gel composition can be placed adjacent to a substantially flat barrier layer that is thereafter shaped so as to yield a treatment device having a desired configuration. The flat barrier layer may have the size of a single oral treatment device, or it may comprise a large sheet from which multiple oral treatment devices can be cut, stamped or otherwise formed.

In the case where the oral treatment composition and/or auxiliary adhesive composition are substantially solid (e.g., a stiff putty or solid), the oral treatment composition and/or auxiliary adhesive composition can be placed inside of a barrier layer already in the form of a dental tray or tray-like configuration. Alternatively, the substantially solid composition can be formed into a desired shape and the barrier layer subsequently attached to an outer surface of the composition.

Notwithstanding the foregoing, it will be appreciated that other manufacturing sequences or procedures may be used to formulate oral treatment devices according to the present invention.

IV. Methods of Using Oral Treatment Devices

The dental bleaching devices according to the invention can be designed to be worn for any desired time period. Increasing the concentration of active agent generally reduces the time required to effect treatment. Nevertheless, due to the extremely comfortable fit and reliable adhesion between the inventive oral treatment devices and the person's teeth, it is possible to wear such devices for extended periods of time in order to ensure more uniform treatment. They may be designed to be worn while performing normal daily activities, such as talking, eating, drinking, smoking, coughing, smiling, frowning, grimacing, yawning, while making virtually any facial expression or mouth contortion, or while sleeping. This greatly decreases their intrusiveness into everyday activities compared to conventional bleaching strips, which do not reliably adhere to teeth, or intrusive treatment devices such as large, bulky bleaching dental appliances.

The oral treatment devices according to the invention may be worn over a person's upper dental arch, lower dental arch, or both simultaneously. The ability to reliably and comfortably wear oral treatment devices over the upper and lower dental arches simultaneously is another departure from bleaching strips, which are not recommended for use in bleaching the upper and lower dental arches at the same time.

Figure 9:
FIG. 9 illustrates a person placing an oral treatment device according to the invention over the upper dental arch.
Figure 10:
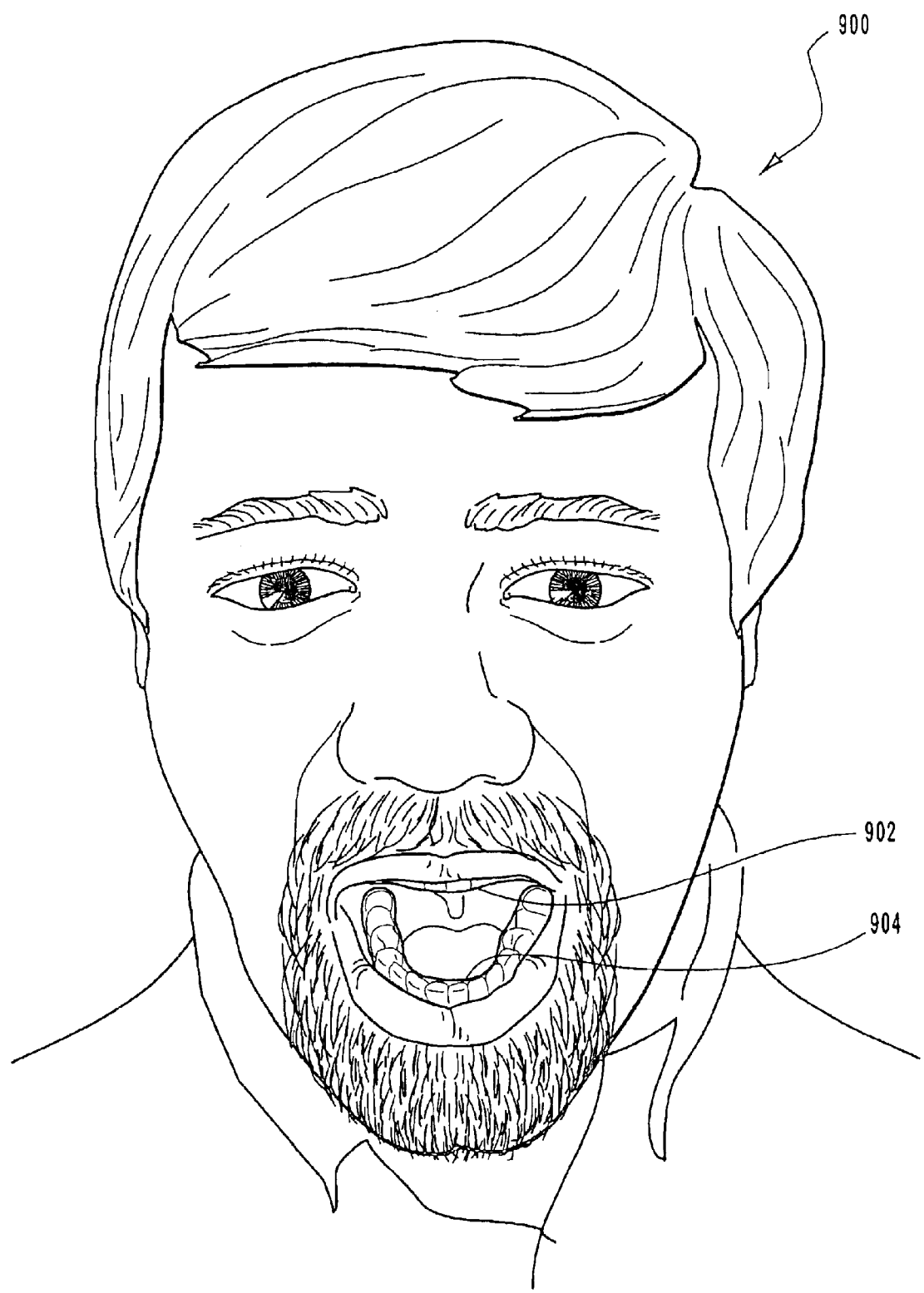
FIG. 10 illustrates a person with oral treatment devices placed over the upper and lower dental arches.

FIG. 9 illustrates a person 900 placing an oral treatment device 902 over the person's upper dental arch. The treatment device 902 can be in the form of a dental tray, having a trough or a device having a tray-like configuration having one or more discontiguous walls that define an interior region that is not a trough. FIG. 10 shows the person 900 with both an oral treatment device 902 over the person's upper dental arch and a treatment device 904 over the lower dental arch. It will be appreciated that the oral treatment devices 902 and 904 can be placed over a person's upper and lower dental arches in any desired order.

To remove the oral treatment device, a user can pry open a corner of the barrier layer using a fingernail or rigid tool and then pull the remainder off. Any residual treatment and/or auxiliary adhesive composition that remains adhered to the person's teeth can be removed by washing or flushing water over the person's teeth, and/or by brushing. Although the inventive treatment and auxiliary adhesive compositions can be very adhesive to teeth when protected from excessive moisture, they can be formulated to quickly break down and dissolve when flushed with excess water and/or by gentle mechanical action (e.g., brushing).

The dental treatment devices can be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional or overnight treatment while a person is sleeping, may last from about 2 hours to about 12 hours.

Treatment sessions according to the invention may be repeated as many times as needed to obtain a desired degree of treatment. In the case of bleaching devices, a clinical whitening effect has been observed after only 1–3 whitening sessions. A typical treatment regimen will preferably include 1–20 treatment sessions, more preferably 2–15 treatment sessions, and most preferably 3–10 treatment sessions.

V. Dental Treatment Kits

For convenience of use, multiple oral treatment devices may be packaged together and sold as a kit. In one embodiment, the number of oral treatment devices provided with each kit may equal the number of sessions that represent a prescribed treatment regimen. Because of the ease of placing the inventive oral treatment devices over a person's teeth, coupled with the reliability with which they adhere to teeth, the likelihood that a particular treatment device will fail, or otherwise not work as intended, is greatly diminished compared to conventional bleaching strips.

To efficiently utilize the space within a kit package, multiple treatment devices can be stacked or interested together. The treatment devices can be sealed collectively or individually as desired. Protective packages 600 and 600' are depicted in FIGS. 6A and 6B. The treatment devices may optionally contain a removable protective layer on an interior surface to protect the treatment composition and auxiliary adhesive composition from contamination or moisture.

It is within the scope of the invention to provide barrier layers, treatment compositions, and auxiliary adhesive compositions that are initially separate and that are brought together by the end user. For example, gel or putty treatment compositions can be expressed or placed adjacent to the barrier layer. The resulting treatment device can be used as is or the treatment composition can be allowed to dry into a solid.

VI. Examples of the Preferred Embodiments

The following are several examples of treatment compositions and auxiliary adhesive compositions that can used in the manufacture of treatment devices according to the invention. The exemplary formulations and manufacturing conditions are given by way of example, not by limitation, in order to illustrate treatment devices that have been found to be useful for treating a person's teeth and/or gums. Unless otherwise indicated, all percentages are by weight.

Examples 1–21 are directed to the manufacture of dental bleaching gel compositions that are processed to yield substantially solid bleaching compositions, used to manufacture treatment devices according to the invention. Examples 22–26 are directed to the manufacture of dental desensitizing compositions that are processed to yield substantially solid desensitizing compositions used to manufacture treatment devices according to the invention. Examples 27–29 are directed to the manufacture of medicament compositions that are processed to yield substantially solid medicament compositions used to manufacture treatment devices according to the invention. Examples 30–37 are directed to the manufacture of auxiliary adhesive compositions that do not include any active agent. Examples 38–43 are directed to sticky, viscous dental bleaching gels that are suitable for use in manufacturing oral treatment devices according to the invention. Examples 44–49 describe further variations of exemplary compositions and devices according to the invention.

EXAMPLE 1

A dental bleaching composition was formed by mixing together the following components:

| | |
|---|---|
| Carbamide Peroxide | 16% |
| Polyvinyl pyrrolidone (M.W. = 1.3 million) | 38% |
| Water | 46% |

The dental bleaching composition was spread in the form of a gel over flexible polymer sheets using a spatula and then heated in a forced air oven heated to a temperature of 50–70° C. for approximately 1 hour. The coated sheets were removed from the oven and inspected. The bleaching gel had dried sufficiently so as to form a substantially solid, coherent bleaching composition on the surface of the polymer sheets. The coated sheets were placed back into the oven overnight to remove additional water.

The coated sheets were removed from the oven a second time, cut apart into smaller-sized pieces, shaped into tray-like devices suitable for placement over a person's teeth.

EXAMPLE 2

A dental bleaching composition was formed by mixing together the following components:

| | |
|---|---|
| Carbamide Peroxide | 16% |
| PolyOx WSR 101 (M.W. = 1 million) | 7% |
| Water | 77% |

The bleaching composition is used to manufacture dental bleaching devices according to the procedures described in Example 1.

EXAMPLE 3

A dental bleaching composition was formed by mixing together the following components:

| | |
|---|---|
| Carbamide Peroxide | 16% |
| Carbopol 974P | 5% |
| Aqueous NaOH (50%) | 6% |
| Water | 73% |

The bleaching composition is used to manufacture dental bleaching devices according to the procedures described in Example 1.

EXAMPLE 4

A dental bleaching composition was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The bleaching composition is used to manufacture dental bleaching devices according to the procedures described in Example 1.

EXAMPLE 5

A dental bleaching composition was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The bleaching composition is used to manufacture dental bleaching devices according to the procedures described in Example 1.

EXAMPLE 6

A dental bleaching composition was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

The bleaching composition is used to manufacture dental bleaching devices according to the procedures described in Example 1.

EXAMPLE 7

A dental bleaching composition was formed by mixing together the following components:

| | |
|---|---|
| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The bleaching composition is used to manufacture dental bleaching devices according to the procedures described in Example 1.

EXAMPLE 8

A dental bleaching composition was formed by mixing together the following components:

| | |
|---|---|
| Carbamide Peroxide | 10% |
| Ethanol | 65% |
| Kollidon VA 90 F (M.W. = 1.3 million) | 20% |
| PEG 600 | 5% |

The bleaching composition is used to manufacture dental bleaching devices according to the procedures described in Example 1.

EXAMPLE 9

A dental bleaching composition was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The bleaching composition is used to manufacture dental bleaching devices according to the procedures described in Example 1.

EXAMPLE 10

A dental bleaching composition was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The bleaching composition is used to manufacture dental bleaching devices according to the procedures described in Example 1.

EXAMPLE 11

A dental bleaching composition was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The bleaching composition is used to manufacture dental bleaching devices according to the procedures described in Example 1.

EXAMPLE 12

A dental bleaching composition was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The bleaching composition is used to manufacture dental bleaching devices according to the procedures described in Example 1.

EXAMPLE 13

A dental bleaching composition was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The bleaching composition is used to manufacture dental bleaching devices according to the procedures described in Example 1.

EXAMPLE 14

A dental bleaching composition was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The bleaching composition is used to manufacture dental bleaching devices according to the procedures described in Example 1.

EXAMPLE 15

A dental bleaching composition was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The bleaching composition is used to manufacture dental bleaching devices according to the procedures described in Example 1.

EXAMPLE 16

A dental bleaching composition was formed by mixing together the following components:

| | |
|---|---|
| Carbamide Peroxide | 15% |
| Polyvinyl pyrrolidone (M.W. = 1.3 million) | 32% |
| Water | 12.8% |
| Ethanol | 20% |
| Glycerin | 10% |
| Aerosil 200 | 5% |
| Calcium EDTA | 0.2% |
| Sodium Lauryl Sulfate | 5% |

The bleaching composition is used to manufacture dental bleaching devices according to the procedures described in Example 1.

EXAMPLE 17

A dental bleaching composition was formed by mixing together the following components:

| | |
|---|---|
| Carbamide Peroxide | 15% |
| Polyvinyl pyrrolidone (M.W. = 1.3 million) | 26% |
| Water | 16.8% |
| Ethanol | 25% |
| Glycerin | 15% |
| Calcium EDTA | 0.2% |
| Sodium Lauryl Ether Sulfate | 2% |

The bleaching composition is used to manufacture dental bleaching devices according to the procedures described in Example 1.

EXAMPLE 18

A dental bleaching composition was formed by mixing together the following components:

| | |
|---|---|
| Carbamide Peroxide | 15% |
| Polyvinyl pyrrolidone (M.W. = 1.3 million) | 32% |
| Water | 13.8% |
| Ethanol | 20% |
| Glycerin | 12% |
| Aerosil 200 | 5% |
| Calcium EDTA | 0.2% |
| Silwet L-7001 | 2% |

The bleaching composition is used to manufacture dental bleaching devices according to the procedures described in Example 1.

EXAMPLE 19

A dental bleaching composition was formed by mixing together the following components:

| | |
|---|---|
| Calcium Peroxide | 20% |
| Carbamide Peroxide | 4% |
| Polyvinyl pyrrolidone (M.W. = 1.3 million) | 20% |
| Water | 11.8% |
| Ethanol | 20% |
| Glycerin | 18% |
| Aerosil 200 | 5% |
| Calcium EDTA | 0.2% |
| Sodium Lauryl Sulfate | 2% |

The bleaching composition is used to manufacture dental bleaching devices according to the procedures described in Example 1.

EXAMPLE 20

A dental bleaching composition was formed by mixing together the following components:

| | |
|---|---|
| Carbamide Peroxide | 10% |
| Kollidon 90 (M.W. = 1.3 million) | 18.7% |
| Water | 42.3% |
| Ethanol | 13.3% |
| Glycerin | 12% |
| Aerosil 200 | 3.3% |
| Sodium Lauryl Sulfate | 0.33% |

The bleaching composition is used to manufacture dental bleaching devices according to the procedures described in Example 1.

EXAMPLE 21

A dental bleaching composition was formed by mixing together the following components:

| | |
|---|---|
| Carbamide Peroxide | 7.1% |
| Kollidon 90 (M.W. = 1.3 million) | 25% |
| Water | 10.7% |
| Ethanol | 50.7% |
| Glycerin | 2.9% |
| Aerosil 200 | 3.6% |

The bleaching composition is used to manufacture dental bleaching devices according to the procedures described in Example 1.

EXAMPLE 22

A dental desensitizing composition suitable for use in making an oral treatment and/or protective auxiliary adhesive composition was formed by mixing together the following components:

| | |
|---|---|
| Sodium Fluoride | 0.25% |
| Polyvinyl pyrrolidone (M.W. = 1.3 million) | 30% |
| Water | 69.75% |

The desensitizing composition was spread in the form of a gel over flexible polymer sheets using a spatula and then heated in a forced air oven heated to a temperature of 50–70° C. for approximately 1 hour. The coated sheets were removed from the oven and inspected. The desensitizing gel had dried sufficiently so as to form a substantially solid, coherent desensitizing composition on the surface of the polymer sheets. The coated sheets were cut apart into smaller-sized pieces and shaped into tray-like devices suitable for placement over a person's teeth.

A bead of bleaching gel is placed over a portion of the substantially solid desensitizing composition so that a portion of the desensitizing composition extends beyond the bleaching composition near one or both rims of a tray-like device to yield a bleaching device according to the invention. The desensitizing composition that extends beyond the bleaching composition forms a protective adhesive region. The bleaching device is used as is or further heated to yield a substantially solid bleaching composition.

Alternatively, a bleaching composition is placed over a portion of the desensitizing composition described initially (i.e., before heating in the forced air oven) to form a dental bleaching device that is used as is or further heated to cause at least a portion of the bleaching composition and desensitizing composition to become substantially solid. The desensitizing composition that extends beyond the bleaching composition, whether in gel or substantially solid form, forms a protective adhesive region.

EXAMPLE 23

A dental desensitizing composition suitable for use in making an oral treatment composition or a protective auxiliary adhesive composition was formed by mixing together the following components:

| | |
|---|---|
| Sodium Citrate | 5% |
| Polyvinyl pyrrolidone (M.W. = 1.3 million) | 20% |
| Water | 75% |

The desensitizing composition is used alone or with a dental bleaching composition to manufacture treatment devices according to the procedures described in Example 22.

EXAMPLE 24

A dental desensitizing composition suitable for use in making an oral treatment composition or a protective auxiliary adhesive was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The desensitizing composition is used alone or with a dental bleaching composition to manufacture treatment devices according to the procedures described in Example 22.

EXAMPLE 25

A dental desensitizing composition suitable for use in making an oral treatment composition or a protective auxiliary adhesive composition was formed by mixing together the following components:

| | |
|---|---|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The desensitizing composition is used alone or with a dental bleaching composition to manufacture treatment devices according to the procedures described in Example 22.

EXAMPLE 26

A dental desensitizing composition suitable for use in making an oral treatment composition or a protective auxiliary adhesive composition was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The desensitizing composition is used alone or with a dental bleaching composition to manufacture treatment devices according to the procedures described in Example 22.

EXAMPLE 27

A medicament composition suitable for use in making an oral treatment composition or a protective auxiliary adhesive was formed by mixing together the following components:

| | |
|---|---|
| Chlorhexidine Gluconate | 2% |
| Polyvinyl pyrrolidone (M.W. = 1.3 million) | 30% |
| Ethanol | 33% |
| Water | 35% |

The medicament composition is used alone or in combination with a dental bleaching composition to manufacture treatment devices according to the procedures described in Example 22.

EXAMPLE 28

A medicament composition suitable for use in making an oral treatment composition or a protective auxiliary adhesive was formed by mixing together the following components:

| | |
|---|---|
| Cetylpyridinium Chloride | 2% |
| Ethanol | 28% |
| Polyvinyl pyrrolidone (M.W. = 1.3 million) | 35% |
| Water | 35% |

The desensitizing composition is used alone or with a dental bleaching composition to manufacture treatment devices according to the procedures described in Example 22.

EXAMPLE 29

A medicament composition suitable for use in making an oral treatment composition or a protective auxiliary adhesive was formed by mixing together the following components:

| | |
|---|---|
| Phenol | 3% |
| Polyvinyl pyrrolidone (M.W. = 1.3 million) | 35% |
| Ethanol | 62% |

The desensitizing composition is used alone or with a dental bleaching composition to manufacture treatment devices according to the procedures described in Example 22.

EXAMPLE 30

An adhesive composition suitable for use in making an auxiliary adhesive composition was formed by mixing together the following components:

| | |
|---|---|
| Water | 25% |
| Ethanol | 30% |
| Glycerin | 10% |
| Polyvinyl pyrrolidone (M.W. = 1.3 million) | 30% |
| Aerosil 200 | 5% |

The adhesive composition and an oral treatment composition are used to manufacture oral treatment devices.

EXAMPLE 31

An adhesive composition suitable for use in making an auxiliary adhesive composition was formed by mixing together the following components:

| | |
|---|---|
| Water | 20% |
| Ethanol | 30% |
| Glycerin | 15% |
| Polyvinyl pyrrolidone (M.W. = 1.3 million) | 30% |
| Aerosil 200 | 5% |

The adhesive composition and an oral treatment composition are used to manufacture treatment devices.

EXAMPLE 32

An adhesive composition suitable for use in making a protective adhesive composition was formed by mixing together the following components:

| | |
|---|---|
| Water | 20% |
| Ethanol | 40% |
| Glycerin | 10% |
| Polyvinyl pyrrolidone (M.W. = 1.3 million) | 30% |

The adhesive composition and an oral treatment composition are used to manufacture treatment devices.

EXAMPLE 33

An adhesive composition suitable for use in making a protective adhesive composition was formed by mixing together the following components:

| | |
|---|---|
| Ethanol | 60.6% |
| Glycerin | 5.1% |
| Polyvinyl pyrrolidone (M.W. = 1.3 million) | 30% |
| Aerosil 200 | 4.3% |

The adhesive composition and an oral treatment composition are used to manufacture treatment devices.

EXAMPLE 34

An adhesive composition suitable for use in making a protective adhesive composition was formed by mixing together the following components:

| | |
|---|---|
| Ethanol | 61.9% |
| Glycerin | 9.5% |
| Polyvinyl pyrrolidone (M.W. = 1.3 million) | 23.8% |
| Aerosil 200 | 4.8% |

The adhesive composition and an oral treatment composition are used to manufacture treatment devices.

EXAMPLE 35

An adhesive composition suitable for use in making a protective adhesive composition was formed by mixing together the following components:

| | |
|---|---|
| Ethanol | 63.6% |
| Glycerin | 9.1% |
| Polyvinyl pyrrolidone (M.W. = 1.3 million) | 27.3% |

The adhesive composition and an oral treatment composition are used to manufacture treatment devices.

EXAMPLE 36

An adhesive composition suitable for use in making a protective adhesive composition was formed by mixing together the following components:

| | |
|---|---|
| Ethanol | 44% |
| Polyvinyl pyrrolidone (M.W. = 1.3 million) | 34% |
| Glycerin | 14% |
| Sodium Lauryl Sulfate | 3% |
| Sucralose | 1% |
| Artificial Peach Flavor | 4% |

The adhesive composition and an oral treatment composition are used to manufacture treatment devices.

EXAMPLE 37

A desensitizing and remineralizing composition suitable for use in making a protective adhesive composition was formed by mixing together the following components:

| | |
|---|---|
| Ethanol | 31.95% |
| Water | 10% |
| Polyvinyl pyrrolidone (M.W. > 1 million) | 27% |
| Polyvinyl pyrrolidone (M.W. ≈ 60,000) | 10% |
| Sodium Lauryl Sulfate | 0.5% |
| Glycerin | 15% |
| Sucralose (25% solution) | 0.5% |
| Peach Flavor | 4% |
| Potassium Nitrate | 0.8% |
| Sodium Fluoride | 0.25% |

The medicament composition is used alone or in combination with a dental bleaching composition to manufacture treatment devices.

EXAMPLE 38

A sticky, viscous dental bleaching gel suitable for use in manufacturing dental bleaching devices according to the invention was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 (SiO$_2$) | 7% |
| Peach Flavor | 2% |
| Polyethylene Glycol (M.W. = 20,000) | 20% |

The dental bleaching gel was placed within a flexible, thin-walled dental tray. The bleaching device is used as is or processed so at to remove a portion of the solvent within the bleaching gel to form a putty or solid. Alternatively, the bleaching gel is used in combination with an auxiliary adhesive composition according to any of Examples 22–37. The bleaching gel and/or auxiliary adhesive composition serve as an endoskeleton.

EXAMPLE 39

A sticky, viscous dental bleaching gel suitable for use in manufacturing dental bleaching devices according to the invention was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The bleaching gel and optionally an auxiliary adhesive composition are used to manufacture dental bleaching devices according to one or more procedures described in Examples 1, 22 and 38.

EXAMPLE 40

A sticky, viscous dental bleaching gel suitable for use in manufacturing dental bleaching devices according to the invention was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The bleaching gel and optionally an auxiliary adhesive composition are used to manufacture dental bleaching devices according to one or more procedures described in Examples 1, 22 and 38.

EXAMPLE 41

A sticky, viscous dental bleaching gel suitable for use in manufacturing dental bleaching devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The bleaching gel and optionally an auxiliary adhesive composition are used to manufacture dental bleaching devices according to one or more procedures described in Examples 1, 22 and 38.

EXAMPLE 42

A sticky, viscous dental bleaching gel suitable for use in manufacturing dental bleaching devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90 F | 2% |
| Carboxy Methyl Cellulose | 5% |
| Peppermint Oil | 1% |

The bleaching gel and optionally an auxiliary adhesive composition are used to manufacture dental bleaching devices according to one or more procedures described in Examples 1, 22 and 38.

EXAMPLE 43

A sticky, viscous dental bleaching gel suitable for use in manufacturing dental bleaching devices according to the invention was formed by mixing together the following components:

| | |
|---|---|
| Water | 22.5% |
| EDTA | 0.1% |
| Carbamide Peroxide | 18.5% |
| Sucralose (25% in water) | 0.75% |
| Glycerin | 41.6% |
| CARBOPOL 974 | 5.3% |
| NaOH (50% in water) | 2.25% |
| Polyvinyl Pyrrolidone (M.W. > 1 million) | 2% |
| Carboxy Methyl Cellulose | 4% |
| Flavor (peach, watermelon or peppermint) | 3% |

The bleaching gel and optionally an auxiliary adhesive composition are used to manufacture dental bleaching devices according to one or more procedures described in Examples 1, 22 and 38.

EXAMPLE 44

Any of the dental bleaching compositions of Examples 1–21 and 38–43 are used together with any of the treatment or auxiliary adhesive compositions of Examples 22–37 to form oral treatment devices according to the invention.

EXAMPLE 45

Any of the treatment or auxiliary adhesive compositions of Examples 22–37 used to manufacture bleaching devices according to Example 44 are modified by adding a bleaching agent in an amount that is less than the amount of bleaching agent within the bleaching a composition manufactured according to one or more of Examples 1–21 and 38–43.

EXAMPLE 46

Any of the dental bleaching compositions of Examples 1–21 and 38–43 use manufacture treatment devices according to Examples 44 and 38–44 are modified by adding one or more of a desensitizing agent, remineralizing agent, antimicrobial agent, antiplaque agent, anti-tartar gent, or other medicament.

EXAMPLE 47

Any of the treatment or adhesive compositions of Examples 22–37 used to manufacture treatment devices according to Examples 22–37 and 44 are modified by adding one or more of a colorant, gingival soothing agent, isotonic solution-forming salt, anesthetic, antioxidant, flavoring agent, preservative, mouth freshening agent, detergent, inorganic thickening agent, remineralizing agent, antiplaque agent, anti-tartar agent, freshening agent, or antioxidant.

EXAMPLE 48

Any of the treatment devices manufactured according to Examples 1–46 are modified by providing a barrier layer in the form of a tray or tray-like device comprising a blend of ethyl vinyl acetate (80%) and polypropylene (20%).

EXAMPLE 49

Any of the treatment or adhesive compositions according to Examples 22–37 are modified by adding an effective amount of one or more bleaching agent activators (e.g., 5% of a an alkali metal or alkaline earth metal base and/or 1% of a metal, metal compound or organo-metallic enzyme).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oral treatment device, comprising:
   a thin, flexible barrier layer in the shape of a dental tray; and
   an oral treatment composition comprising an active agent and a tissue adhesion agent,
      said oral treatment composition having a consistency in a range from a sticky, viscous gel to a solid composition,
      said oral treatment composition acting as an endoskeleton so as to at least partially contribute to maintaining said barrier layer in the shape of a dental tray prior to use,
      said oral treatment composition being sticky and adhesive during use so as to cause said barrier layer to at least partially conform to a person's tooth surfaces during use.

2. An oral treatment device as defined in claim 1 said barrier layer being so flexible as to be incapable of maintaining the shape of a dental tray in the absence of said oral treatment composition prior to use.

3. An oral treatment device as defined in claim 2, said oral treatment composition preventing a front sidewall and a bottom wall from collapsing together and/or spreading apart prior to use.

4. An oral treatment device as defined in claim 1, said barrier layer having a thickness in a range of about 0.0001 inch to about 0.012 inch.

5. An oral treatment device as defined in claim 1, said barrier layer having a thickness in a range of about 0.001 inch to about 0.01 inch.

6. An oral treatment device as defined in claim 1, wherein said oral treatment composition comprises a bead.

7. An oral treatment device as defined in claim 6, wherein said bead has a cross-sectional diameter in range of about 1 mm to about 5 mm.

8. An oral treatment device as defined in claim 6, wherein said bead has a cross-sectional diameter in a range of about 2 mm to about 4 mm.

9. An oral treatment device as defined in claim 1, wherein said oral treatment composition comprises a continuous layer on an inner surface of the barrier layer.

10. An oral treatment device as defined in claim 9, wherein said continuous layer has a thickness in a range of about 0.25 mm to about 2 mm.

11. An oral treatment device as defined in claim 9, wherein said contiguous layer has a thickness in a range of about 0.5 mm to about 1 mm.

12. An oral treatment device as defined in claim 1, wherein said oral treatment composition is a sticky and viscous composition having a glue-like consistency.

13. An oral treatment device as defined in claim 1, wherein said oral treatment composition is a stiff putty that is substantially solid but malleable and that becomes stickier and more adhesive to a person's teeth and/or gun's when moistened with saliva or water.

14. An oral treatment device as defined in claim 1, wherein said barrier layer includes a front sidewall and a bottom sidewall that are contiguous so as to form a trough into which said oral treatment composition is placed prior to use.

15. An oral treatment device as defined in claim 1, wherein said barrier layer includes a front sidewall and a noncontiguous bottom wall that includes cuts or discontinuities so as to form a plurality of bottom flaps that are more easily conformable to inner surfaces of adjacent teeth having varying widths.

16. An oral treatment device as defined in claim 1, said barrier layer comprising at least one of wax, metal foil, paraffin, ethylene-vinyl acetate copolymer, ethylene-vinyl alcohol copolymer, polycaprolactone, polyolefin, polyethylene, high density polyethylene, low density polyethylene, ultra-low density polyethylene, polypropylene, polytetrafluoroethylene, polyester, polycarbonate, polyurethane, polyamide, or polyesteramide.

17. An oral treatment device as defined in claim 1, further comprising a removable exoskeleton that helps maintain said barrier layer in the shape of a dental tray prior to use.

18. An oral treatment device as defined in claim 1, said barrier layer designed so as to approximately terminate at or near a person's gingival margin during use.

19. An oral treatment device as defined in claim 1, said barrier layer designed so as to overlap a person's gingival margin during use.

20. An oral treatment device as defined in claim 1, said tissue adhesion agent comprising at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

21. An oral treatment device as defined in claim 1, said treatment composition comprising at least one active agent selected from the group comprising dental bleaching agents, dental desensitizing agents, anesthetics, gingival soothing agents, stabilizing agents, remineralizing agent, antimicrobial agents, antiplaque agents, anti-tartar agents, mouth freshening agents, and anti-oxidants.

22. An oral treatment device as defined in claim 1, further comprising an auxiliary adhesive composition.

23. A kit for use in treating a person's teeth and/or gums comprising a plurality of said oral treatment devices according to claim 1.

24. A method for treating a person's teeth and/or gums comprising obtaining an oral treatment device according to claim 1 and placing it over at least a portion of tho person's teeth and/or gums for a desired time period.

25. A dental bleaching device, comprising:
   a thin, flexible barrier layer in the shape of a dental tray; and
   a dental bleaching composition comprising a dental bleaching agent and a tissue adhesion agent,
      said dental bleaching composition having a consistency in a range from a sticky, viscous gel to a solid composition,
      said dental bleaching composition acting as an endoskeleton so as to at least partially contribute to maintaining said barrier layer in the shape of a dental tray prior to use
      said dental bleaching composition being sticky and adhesive during use so as to cause said barrier layer to at least partially conform to a person's tooth surfaces during use.

26. A dental bleaching device as defined in claim 25, said barrier layer being so flexible as to be incapable of maintaining the shape of a dental tray in the absence of said dental bleaching composition prior to use.

27. A dental bleaching device as defined in claim 25, said barrier layer having a thickness in a range of about 0.001 inch to about 0.01 inch.

28. A dental bleaching device as defined in claim 25, wherein said dental bleaching composition is a sticky and viscous composition having a glue-like consistency.

29. A dental bleaching device as defined in claim 25, wherein said dental bleaching composition is a sticky putty that is substantially solid but malleable and that becomes stickier and more adhesive to a person's teeth and/or gums when moistened with saliva or water.

30. An oral treatment device, comprising:
   a thin, flexible barrier layer in the shape of a dental tray and having a thickness in a range of about 0.001 inch to about 0.01 inch; and
   an oral treatment composition comprising a tissue adhesion agent and at least one of a dental bleaching agent or a tooth desensitization agent,
      said oral treatment composition having a consistency in a range from a sticky, viscous gel to a solid composition,
      said oral treatment composition acting as en endoskeleton so as to at least partially contribute to maintaining said barrier layer in the shape of a dental tray prior to use,
      said oral treatment composition being sticky and adhesive during use so as to cause said barrier layer to at least partially conform to a person's tooth surfaces during use.

31. An oral treatment device as defined in claim 30, wherein said oral treatment composition is a sticky and viscous composition having a glue-like consistency.

32. An oral treatment device as defined in claim 30, wherein said oral treatment composition is a stiff putty that is substantially solid but malleable and that becomes stickier and more adhesive to a person's teeth and/or gums when moistened with saliva or water.

* * * * *

UNITED STATES PATENT AND TRADEMARK OFFICE
CERTIFICATE OF CORRECTION

PATENT NO. : 6,860,736 B2
DATED : March 1, 2005
INVENTOR(S) : Peter M. Allred and Dan E. Fischer It is certified that error appears in the above-identified patent and that said Letters Patent is hereby corrected as shown below:

Title page,
Item [56], References Cited, OTHER PUBLICATIONS, insert entry -- Technical Bulletin: Hydrogen Peroxide-Polyvinylpyrrolidone Polymer Complexes, International Specialty Products, 1361 Alps Road, Wayne, New Jersey 07470, www.ispcorp.com (Dec. 2003) --.

Column 8,
Line 40, change "try" to -- tray --.

Column 14,
Line 44, change "700'0" to -- 700' --.
Line 55, change "800"" to -- 800' --.

Column 17,
Line 3, after "compositions that can" insert -- be --.

Column 29,
Line 43, before "manufacture" change "use" to -- used to --.
Line 44, change "44" to -- 1-21 --.
Line 46, change "gent" to -- agent --.

Column 30,
Line 2, before "an alkali" remove "a".
Line 66, change "gun's" to -- gums --.

Column 31,
Line 51, change "tho" to -- the --.

UNITED STATES PATENT AND TRADEMARK OFFICE
CERTIFICATE OF CORRECTION

PATENT NO. : 6,860,736 B2
DATED : March 1, 2005
INVENTOR(S) : Peter M. Allred and Dan E. Fischer It is certified that error appears in the above-identified patent and that said Letters Patent is hereby corrected as shown below:

Column 32,
Line 38, change "en" to -- an --.

Signed and Sealed this

Thirtieth Day of August, 2005

JON W. DUDAS
*Director of the United States Patent and Trademark Office*